(12) United States Patent
Klem et al.

(10) Patent No.: US 10,524,110 B1
(45) Date of Patent: Dec. 31, 2019

(54) AFFIRMATIVE PAIRING SYSTEMS AND METHODS FOR DEVICES

(71) Applicant: Roche Diabetes Care, Inc., Indianapolis, IN (US)

(72) Inventors: Kurt Klem, Indianapolis, IN (US); Craig Carlson, Fishers, IN (US); Joe Forler, Zionsville, IN (US); Tim Aykroyd, Carmel, IN (US); Eric Williams, Fishers, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 16/135,557

(22) Filed: Sep. 19, 2018

(51) Int. Cl.
*H04W 8/00* (2009.01)
*H04L 29/06* (2006.01)
*H04W 12/08* (2009.01)

(52) U.S. Cl.
CPC ......... *H04W 8/005* (2013.01); *H04L 63/0492* (2013.01)

(58) Field of Classification Search
CPC ..... H04W 8/005; H04W 76/14; H04W 12/06; H04W 92/18; H04L 63/0492
USPC ...................................................... 455/41.2
See application file for complete search history.

(56) References Cited

U.S. PATENT DOCUMENTS

| 9,338,638 | B1* | 5/2016 | Palin | H04W 12/06 |
| 2012/0142271 | A1* | 6/2012 | Zhodzishsky | H04L 67/303 455/41.2 |
| 2014/0327319 | A1* | 11/2014 | Byun | H02J 7/025 307/104 |
| 2017/0286028 | A1* | 10/2017 | Yang | G06F 3/1203 |

* cited by examiner

*Primary Examiner* — Lee Nguyen
(74) *Attorney, Agent, or Firm* — Dinsmore & Shohl, LLP

(57) ABSTRACT

Methods and systems for a device pairing system configured to pair and including a peripheral device (PD) and a central device (CD), and memory communicatively coupled to processor(s) and storing instructions that cause the system to perform when executed by processor(s): establishing a connection over a wireless communication channel between the devices; conducting, by the CD, a discovery of a characteristic value of the PD; determining an authentication determination prior to device pairing based on determination of a central characteristic value to arrive at one of a successful determination and an unsuccessful determination; utilizing the CD to send a pairing request to the PD to initiate pairing over the wireless communication channel based upon the characteristic discovery of the characteristic value of the PD; and, in response to the successful determination as the authentication determination, approving the pairing request with the PD and sending a pairing response to the CD.

25 Claims, 11 Drawing Sheets

AFFIRMATIVE PAIRING SYSTEMS AND METHODS FOR DEVICES

TECHNICAL FIELD

The present specification generally relates to affirmative device pairing systems and methods for devices to complete a wireless communication pairing between a pair of wireless devices and, more specifically, to affirmative device pairing systems to complete an authenticated wireless communication pairing between medical devices and methods of use of such systems.

BACKGROUND

A large population of wireless communication devices exists in the market, particularly those which communicate via a wireless communication such as BLUETOOTH® communication. When devices attempt to pair through a BLUETOOTH® pairing procedure, it is possible for an unintended wireless device to interfere and even prevent an intended pairing between a central device and a peripheral device.

Accordingly, a need exists for alternative systems and methods of use to permit wireless communication pairing in a manner that prevents interferences from such unintended devices as possible connection points, which may otherwise connect to a peripheral device and disrupt an intended pairing.

SUMMARY

In one embodiment, a device pairing system may include a peripheral device, a central device, one or more processors, one or more memory components communicatively coupled to the one or more processors, and machine readable instructions stored in the one or more memory components. The device pairing system may be configured to pair the peripheral device and the central device to establish a paired wireless communication channel therebetween. The machine readable instructions may cause the device pairing system to perform at least the following when executed by the one or more processors: establish a connection over a wireless communication channel between the peripheral device and the central device; conduct, by the central device, a GATT characteristic discovery of a GATT characteristic value of a GATT service of the peripheral device over the wireless communication channel; determine an authentication determination prior to device pairing based on determination of a central GATT characteristic value to arrive at one of a successful match determination and an unsuccessful match determination; utilize the central device to send a pairing request to the peripheral device to initiate pairing over the wireless communication channel based upon the GATT characteristic discovery of the GATT characteristic value of the GATT service of the peripheral device. The instructions may further cause the device pairing system to: in response to the unsuccessful match determination as the authentication determination, reject the pairing request with the peripheral device; in response to the successful match determination as the authentication determination, approve the pairing request with the peripheral device and send a pairing response to the central device; and pair the central device and the peripheral device based on the pairing response to create the paired wireless communication channel.

In another embodiment, device pairing system may include a peripheral device, a central device, the device pairing system configured to pair the peripheral device and the central device to establish a paired wireless communication channel therebetween, one or more processors, one or more memory components communicatively coupled to the one or more processors, and machine readable instructions. The machine readable instructions may be stored in the one or more memory components that cause the device pairing system to perform at least the following when executed by the one or more processors: establish a connection over a wireless communication channel between the peripheral device and the central device; conduct, by the central device, a GATT characteristic discovery of a characteristic value of the peripheral device over the wireless communication channel; send a requested feature from the central device to the peripheral device to determine an authentication determination; determine the authentication determination prior to device pairing based on whether the requested feature received by the peripheral device is correct to arrive at one of a successful determination and an unsuccessful match determination; and utilize the central device to send a pairing request to the peripheral device to initiate pairing over the wireless communication channel based upon the GATT characteristic discovery of the peripheral device and the authentication determination. The instructions may further cause the device pairing system to: in response to an incorrect finding for the authentication determination, reject the pairing request with the peripheral device; in response to a correct finding for the authentication determination, send an initial pairing response by the peripheral device including a security request and proceed to a second authentication determination; determine in the second authentication determination whether the central device exchanged proper security keys with the peripheral device in response to the security request; in response to a negative finding for the second authentication determination, reject the pairing request with the peripheral device; and in response to a positive finding for the second authentication determination, complete the pairing between the peripheral device and the central device to create the paired wireless communication channel.

In yet another embodiment, a device pairing system may include a peripheral device, a central device, the device pairing system configured to pair the peripheral device and the central device to establish a paired wireless communication channel therebetween, one or more processors, and one or more memory components communicatively coupled to the one or more processors. The device pairing system may further include machine readable instructions stored in the one or more memory components that cause the device pairing system to perform at least the following when executed by the one or more processors: establish a connection over a wireless communication channel between the peripheral device and the central device; conduct, by the central device, a GATT characteristic discovery of a characteristic value of the peripheral device over the wireless communication channel; send authentication data from the central device to the peripheral device indicative of a first authentication determination; utilize the central device to send a pairing request to the peripheral device to initiate pairing over the wireless communication channel based upon the first authentication determination; and determine a second authentication determination prior to device pairing based on whether the authentication data to indicate the second authentication is successful or unsuccessful. The instructions may further cause the device pairing system to:

in response to the second authentication determination being unsuccessful, reject the pairing request with the peripheral device; in response to the second authentication determination being successful, approve the pairing request with the peripheral device and send a pairing response to the central device; and pair the central device and the peripheral device based on the pairing response to create the paired wireless communication channel.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
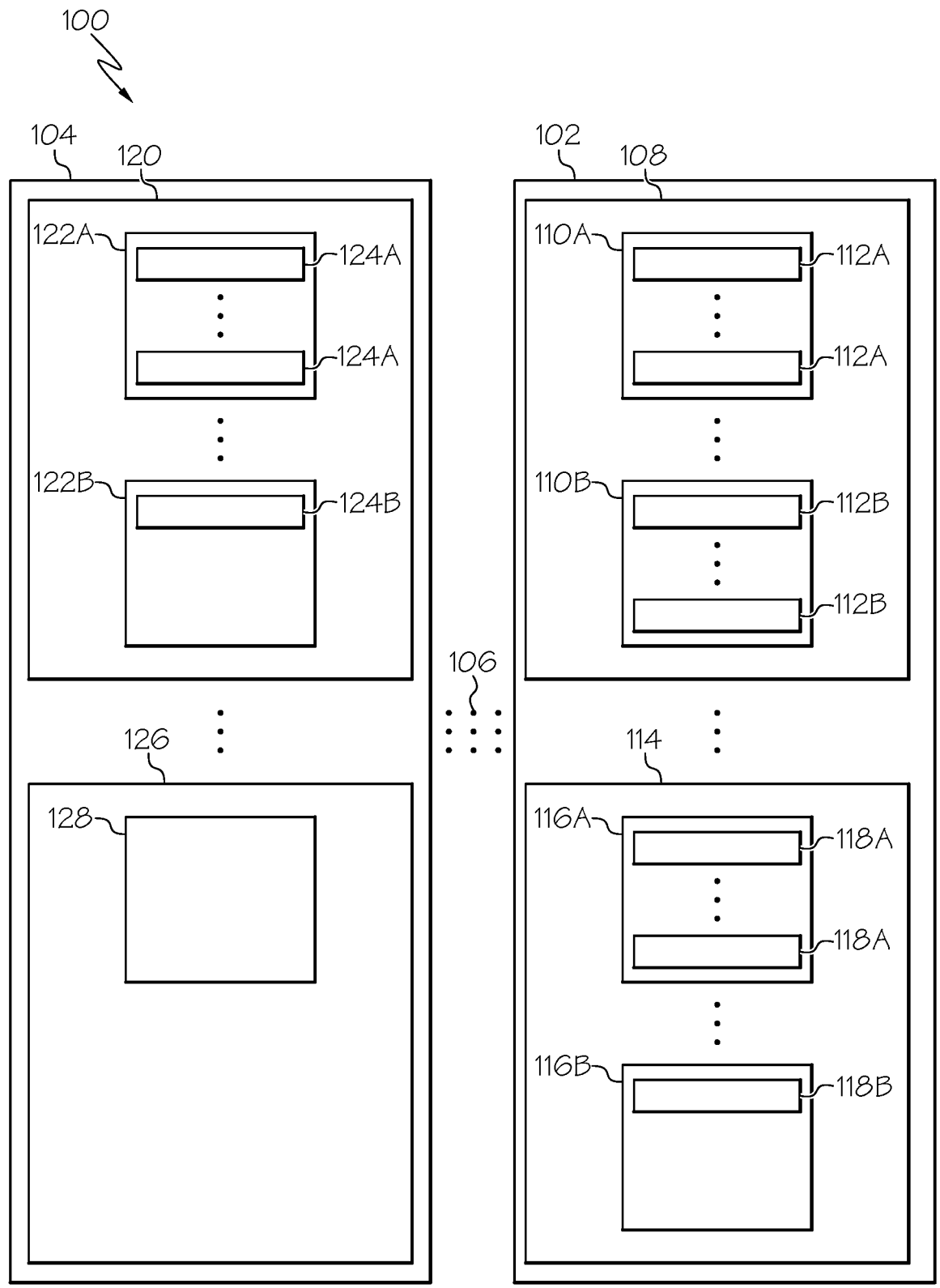
FIG. 1 schematically illustrates a device pairing system for affirmatively pairing a central device and a peripheral device, according to one or more embodiments shown and described herein.

Referring generally to the figures, embodiments of the present disclosure are directed to device pairing systems to pair devices through a paired wireless communication, which may be encrypted, based on success of alternative pairing authentication processes and methods of use of such systems. For example, multiple medical devices are available and provided for multiple worldwide markets and may be configured through a wireless communication scheme, such as a BLUETOOTH® communication following a V4.0 BLUETOOTH® Core Specification and above, to pair with one another. Such medical devices may be utilized by users such as diabetic persons to more effectively manage their diabetic conditions, as described in greater detail further below. When a pair of such medical devices including a peripheral device and a central device attempt to pair through the wireless communication scheme, however, a possibility exists that an unintended wireless device may interfere with and may even prevent the desired device pairing between the peripheral device and the central device. Embodiments of the systems herein describe authentication mechanisms and schemes prior to device pairing that may aid with pre-filtering out such unintended devices to eliminate or reduce a potential for unintended devices to connect with the peripheral device and disrupt the desired pairing between the intended peripheral device and the intended central device. Furthermore, the authentication mechanisms and schemes described herein occurring prior to device pairing assist to improve associated technologies and efficiencies of processing in expediting pairing processes and reducing pairing time for such processes by affirming pairing between devices prior to initiating time consuming pairing steps such that pairing authentication affirmation checks take place before a first pairing request. As will be described in greater detail in embodiments below, such a pairing request may utilize the pairing authentication affirmation check to result in either a rejection of the pairing based on an unsuccessful authentication or a submission of a positive pairing response based on a successful authentication.

Reference will now be made in detail to embodiments of the device pairing systems including such authentication mechanisms, and examples of such systems are illustrated in the accompanying drawings. Wherever possible, the same reference numerals will be used throughout the drawings to refer to the same or like parts. Various embodiments of the medical device data manager configuration systems will be described in further detail herein with specific reference to the appended drawings.

Referring to FIG. 1, a device pairing system 100 includes a pair of devices, one being a peripheral device 102 and the other being a central device 104. The peripheral device 102 and the central device 104 may be a pair of medical devices. Each medical device may be a blood glucose meter, a continuous glucose monitor, an insulin pump, a wellness device, or a like medical device. By way of example and not as a limitation, a wellness device may be a device configured to improve the wellness of an individual through tracking wellness data associated with the health and wellness of the individual and/or monitoring activity of the individual. Such wellness data may include, for example, data indicative of vital signs including heart rate, calories consumed and burned, and cholesterol levels. The monitored activity of the individual may include data indicative of a number of steps taken in a time period or another fitness activity conducted by the individual such as running, cycling, or hiking.

Further, the device pairing system 100 includes at least a processor and a memory communicatively coupled to the processor, such as the one or more processors 1104 and the one or more memory components 1106 as described with respect to FIG. 11 in greater detail further below. The device pairing system 100 includes machine readable instructions stored in the memory that cause the device pairing system 100 to perform one or more of instructions when executed by the processor.

Referring again to FIG. 1, the peripheral device 102 and the central device 104 may communicate through a wireless protocol 106, such as an Attribute Protocol (ATT) used for BLUETOOTH® communication. BLUETOOTH® communication allows devices to communicate without a central device such as a router or access point. BLUETOOTH® communication also utilizes a low energy feature referable to as BLUETOOTH® Low Energy (BLE), such that BLUETOOTH® communication may be used without requiring much power from the devices using BLUETOOTH® communication.

As a non-limiting example, the peripheral device 102 includes a Generic Attribute profile (GATT) used for BLUETOOTH® communication. The GATT for a device using BLUETOOTH® communication is a BLUETOOTH® profile that acts as an interface specification to define data that a device has, what another connecting device may do with such data over a BLUETOOTH® communication and connection, and how the device with the GATT should respond when the connecting device acts upon the data.

The GATT of the peripheral device 102 includes an Attribute Table that is a table of data accessible by other connected devices per various methods of access. The GATT of the peripheral device 102 includes services 108, 114, characteristics 110A, 110B, 116A, 116B, and descriptors 118A, 118B as types of attributes of the Attribute Table. Attributes as described herein each include a type identified by a Universal Unique Identifier (UUID), and one or more attributes may be defined by the BLUETOOTH® Special Interests Group (SIG), which is the technical standards body for BLUETOOTH®. Such defined attributes may have UUIDs that are 16 bits in length. One or more other attributes may be custom designed for a device and have UUIDs that are 128 bits in length. While a service must have one or more characteristics, which are one or more values used by the service, a characteristic does not need to have a descriptor. For the GATT of the peripheral device 102, the service 108 includes characteristics 110A, 110B, which respectively include descriptors 112A, 112B. Additionally, the service 114 includes characteristics 116A, 116B, which respectively include descriptors 118A, 118B.

By way of example and not as a limitation, the services 108, 114 are respectively representative of a particular feature of the peripheral device 102, such as a hardware feature that may be a button or a particular sensor. The service 108 may be, for example, a Device Information Service (DIS) that includes various information about the peripheral device 102, including manufacturer and serial number data and additional information regarding particular device aspects. A DIS is a BLUETOOTH® SIG defined service.

The characteristics 110A, 110B, 116A, 116B are representative of characteristic data that relates to a particular internal state of the peripheral device 102, an environmental state that is measurable by the peripheral device 102 such through a sensor of the peripheral device 102, or configuration data such as setting a frequency at which to make such sensor measurements. As a non-limiting example, a battery level may be representative internal state data, while temperature may be representative environmental state data.

In an embodiment, the characteristics 110A, 110B, 116A, 116B also provide information regarding how such characteristic data is made available to a connecting device, such as the central device 104, to use through a BLUETOOTH® pairing and/or communication. The characteristics 110A, 110B, 116A, 116B may include one or more parts, such as a type, a value, one or more properties, and/or one or more permissions. As a non-limiting example, a UUID value may be indicative what particular type of characteristic an attribute may be, and the value may be representative of the value of a state data item associated with the characteristic. The one or more properties may be definitive of actions another device, such as the central device 104, may take with a characteristic of, for example, the peripheral device 102, over a BLUETOOTH® pairing and/or communication, such as read, write, or notify with respect to the characteristic.

Reading of a characteristic by the central device 104 permits transferring a current characteristic value from an attribute table of the peripheral device 102 to the central device 104. Writing of a characteristic by the central device 104 permits the central device 104 to write to and change the characteristic value in the state table of the peripheral device 102. Notifying permits providing a special message type that a device, such as the peripheral device 102, may send to a connecting device, such as the central device 104, when a characteristic value changes or upon a periodically controlled time interval. The one or more permissions are associated with security features and may describe one or more requisite security conditions prior to granting characteristic read or write access to a device, such as the central device 104.

In an embodiment, the descriptors 112A, 112B, 118A, 118B of the GATT of the peripheral device 102 include metadata that may augment one or more details relating to a respective characteristics 110A, 110B, 116A, 116B to which the descriptors 112A, 112B, 118A, 118B belong or permit configuration of a behavior of the respective characteristics 110A, 110B, 116A, 116B, such as enabling or disabling of notification messages.

As a non-limiting example, the central device 104 also includes a Generic Attribute profile (GATT) used for BLUETOOTH® communication. The GATT of the central device 104 includes an Attribute Table that is a table of data accessible by other connected devices per various methods of access. The GATT of the central device 104 includes services 120, 126, characteristics 122A, 122B, 128, and descriptors 124A, 124B as types of attributes of the Attribute Table. The service 120 includes characteristics 122A, 122B, which respectively include descriptors 124A, 124B. The service 126 includes characteristic 128.

By way of example and not as a limitation, the services 120, 126 are respectively representative of a particular feature of the central device 104, such as a hardware feature that may be a button or a particular sensor. The service 120 may be, for example, a DIS that includes various information about the central device 104, including manufacturer and serial number data.

The characteristics 122A, 122B, 128 are representative of characteristic data that relates to a particular internal state of the central device 104, an environmental state that is measurable by the central device 104 such through a sensor, or configuration data such as setting a frequency at which to make such sensor measurements. In an embodiment, the characteristics 122A, 122B, 128 also provide information regarding how such characteristic data is made available to a connecting device to use through a BLUETOOTH® pairing and/or communication. The characteristics 122A, 122B, 128 may include one or more parts, such as a type, a value, one or more properties, and/or one or more permissions similar to as described above with respect to the characteristics 110A, 110B, 116A, 116B of the GATT of the peripheral device 102.

In an embodiment, the descriptors 124A, 124B of the GATT of the central device 104 include metadata that may augment one or more details relating to respective characteristics 122A, 122B to which the descriptors 124A, 124B belong or permit configuration of a behavior of the respective characteristics 122A, 122B.

Figure 2:
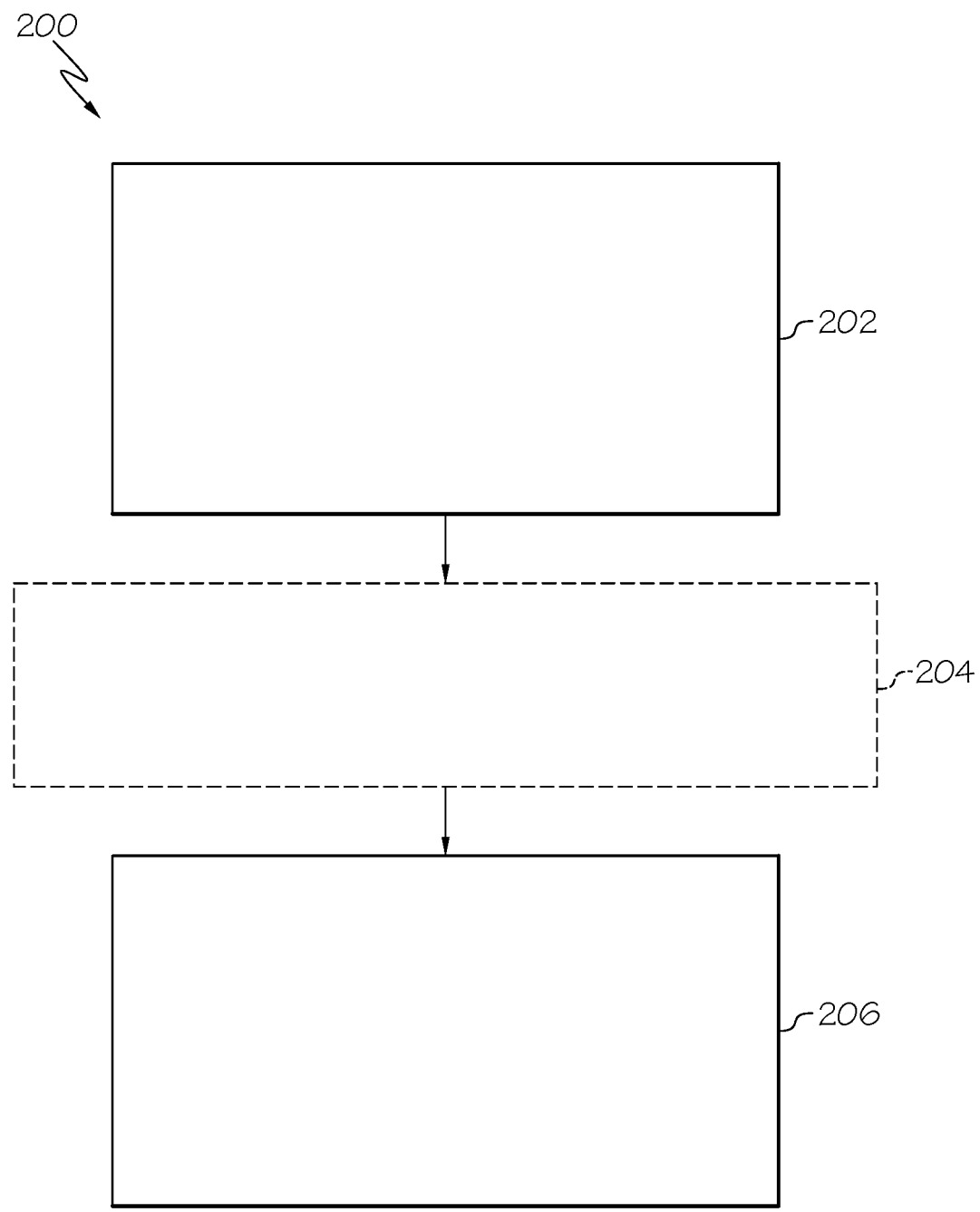
FIG. 2 schematically illustrates a pairing process, including an initial connection stage, an intermediate affirmative pairing stage, and a final device bonding stage, according to one or more embodiments shown and described herein FIG. 3 schematically illustrates a process outlining example steps of the initial connection stage of FIG. 2, according to one or more embodiments shown and described herein.

FIG. 2 illustrates a device pairing and bonding process 200 between the peripheral device 102 and the central device 104, including an initial connection stage 202, an intermediate affirmative pairing stage 204, and a final device bonding stage 206. In at least one embodiment, one or more processors 1104 are configured to perform the device pairing process 200 from the initial connection stage 202 to the final device bonding stage 206, as described in greater detail further below. The one or more processors 1104 are configured to perform, for example, steps of the initial connection stage 202 as further described in with respect to a device discovery process 302 of FIG. 3, the intermediate affirmative pairing stage 204 as further described in with respect to embodiments depicted as affirmative pairing processes 504-1004 of FIGS. 5-10, and a final device bonding stage 206 as further described in with respect to a bonding process 406 of FIG. 4.

Figure 3:
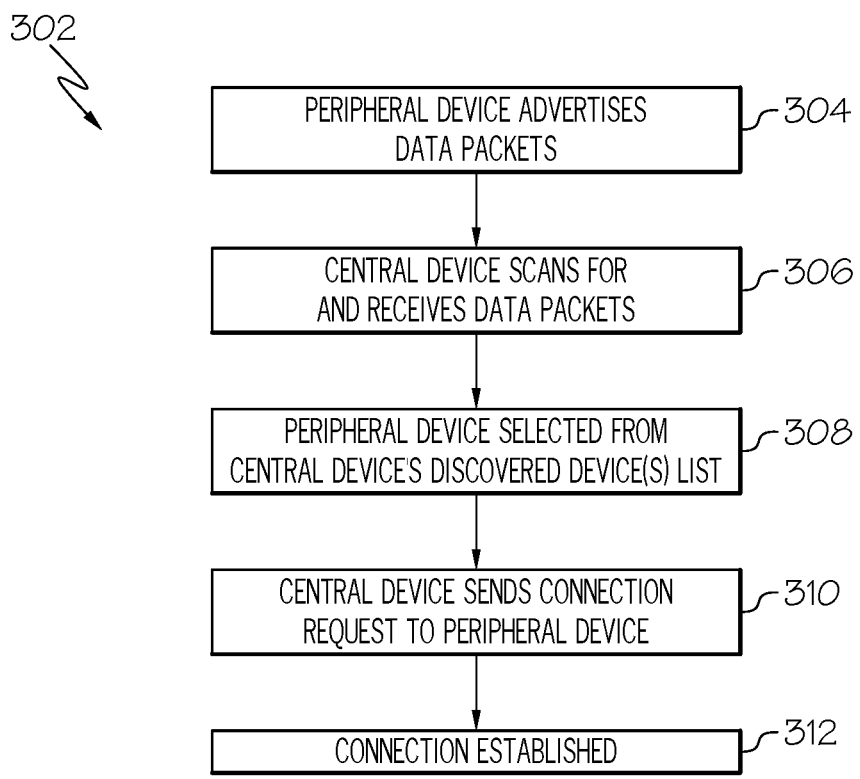

FIG. 3 illustrates a device discovery process 302 that may be implemented as the initial connection stage 202 of FIG. 2. As a non-limiting example, both the peripheral device 102 and the central device 104 are placed in a pairing mode by, for example, a user to initiate the device discovery process 302. In the pairing mode, the peripheral device 102 advertises data packets in block 304. In an embodiment, through use of a Generic Access Profile (GAP) of associated BLUETOOTH® architecture, a user may select a pairing mode option on the peripheral device such that the peripheral device 102 advertises the data packs by emitting data packets periodically, which may be small packets of data. As a non-limiting example, GAP is a layer of the BLUETOOTH® architecture stack that determines network topology of the BLUETOOTH® architecture system. The GAP advertised data packets include information about the peripheral device 102, which may be, for example, device configuration manufacturing data of the peripheral device 102.

Other devices, such as the central device 104, searching for devices with which to connect act as scanning devices configured to scan, receive, and process the data packets being advertised. As a non-limiting example, the peripheral device 102 may be referenced as a GAP peripheral device, and the central device 104 may be reference as a GAP central device configured to initiate connection with the GAP peripheral device.

In block 306, the central device 104 scans for and receives the advertised data packet(s) of the peripheral device 102. The central device 104 rejects and filters out data packets from devices with which the central device 104 is not interested in communicating, such as devices of a particular undesired type as advertised in their respective data packets. In at least one embodiment, a user selects a menu option from the central device 104 to discover devices, and the central device 104 enters a scanning mode to discover devices and sends a scan request. The devices discovered by the central device 104 that send scan response may be within a certain range of the central device 104 based on, for example, a received signal strength indicator (RSSI) measurement of a discoverable device, such as the peripheral device 102.

In block 308, the peripheral device is selected from a discovered device's list of the central device 104. In at least one embodiment, a user may select the peripheral device from the discovered device's list on a display screen of the central device 104 if, for example, multiple devices are found. In block 310, the central device 104 sends a connection request to the selected peripheral device 102. In block 312, a connection is established between the central device 104 and the peripheral device 102. After the connection is established, the central device 104 and the peripheral device 102 may continue on to the intermediate affirmative pairing stage 204 to pair the devices through exchanging information that is necessary to establish an encrypted, paired connection.

After being paired through the intermediate affirmative pairing stage 204, which is described in greater detail below with respect to the embodiments of affirmative pairing processes 504-1004 of FIGS. 5-10, the central device 104 and the peripheral device 102 may perform a bonding process 406 (FIG. 4) as reflected through the final device bonding stage 206 of FIG. 2. In the bonding process 406, information from the intermediate affirmative pairing stage 204 is stored on the central device 104 and the peripheral device 102 such that the intermediate affirmative pairing stage 204 does not need to be repeated each time the central device 104 and the peripheral device 102 connect ongoing.

Figure 4:
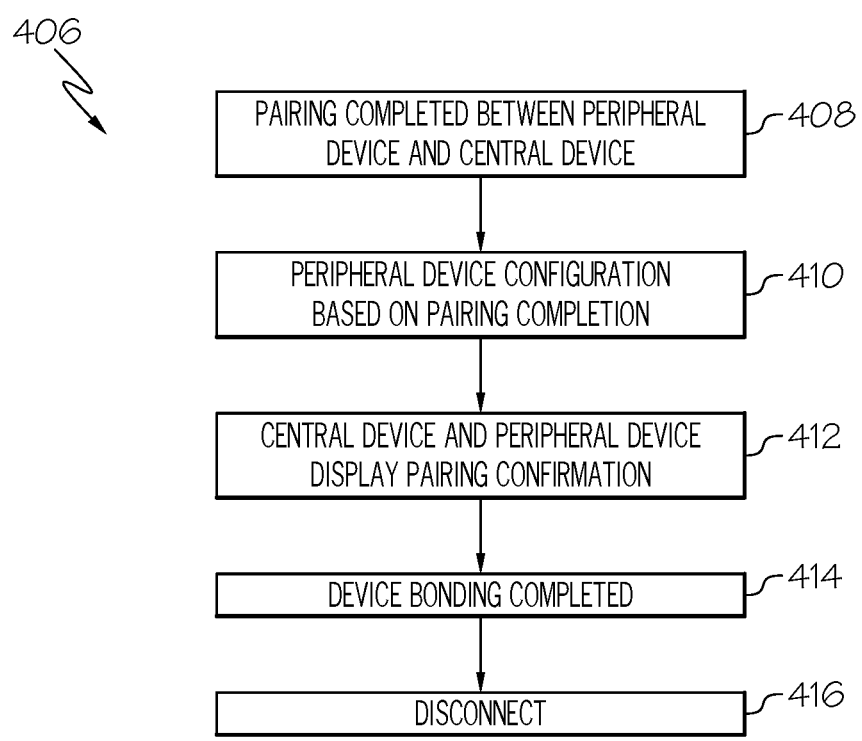
FIG. 4 is a flow chart of a process outlining example steps of the final device bonding stage of FIG. 2, according to one or more embodiments shown and described herein.

FIG. 4 illustrates at least one embodiment of the bonding process 406. In block 408, pairing is completed between the peripheral device 102 and the central device 104 after the intermediate affirmative pairing stage 204 concludes to progress onto the final device bonding stage 206 of FIG. 2. In block 410, a configuration of the now paired peripheral device 102 may occur based on completion of the pairing between the central device 104 and the peripheral device 102. For example, the central device 104 may write to certain characteristics of the paired peripheral device 102 to control and further configure the peripheral device 102.

In block 412, the peripheral device 102 and the central device 104 display a pairing confirmation on respective display screens to indicate a successful pairing between the peripheral device 102 and the central device 104. In block 414, device bonding is completed between the peripheral device 102 and the central device 104. In at least one embodiment, the device bonding permits information from the intermediate affirmative pairing stage 204 to be stored on the central device 104 and the peripheral device 102 such that the intermediate affirmative pairing stage 204 does not need to be repeated each time the central device 104 and the peripheral device 102 connect ongoing after a successful pairing. In block 416, the central device 104 and the peripheral device 102 may be disconnected from one other from either side.

Referring again to FIG. 2, the intermediate affirmative pairing stage 204 is set between the initial connection stage 202 of FIG. 3 and the final device bonding stage 206. The initial connection stage 202 is described in greater detail above with respect to the device discovery process 302 of FIG. 3, and the final device bonding stage 206 is described in greater detail above with respect to the bonding process 406 of FIG. 4. The intermediate affirmative pairing stage 204 is described in greater detail below with respect to the alternative embodiments respectively depicted as the plurality of affirmative pairing processes 504-1004 of FIGS. 5-10.

In at least one embodiment, the device pairing system 100 is configured to implement the plurality of affirmative pairing processes 504-1004 of FIGS. 5-10 and includes the peripheral device 102, the central device 104, one or more processors 1104, one or more memory components 1106 communicatively coupled to the one or more processors 1104, as described in greater detail further below, and machine readable instructions stored in the one or more memory components 1106 that cause the device pairing system 100 to perform and implement at least the plurality of affirmative pairing processes 504-1004 when executed by the one or more processors 1104. The device pairing system 100 is further configured to pair the peripheral device 102 and the central device to establish a paired wireless communication channel therebetween.

As a non-limiting example, FIGS. 5-6 respectively illustrate GATT based affirmative pairing processes as a GATT read-based affirmative pairing process 504 in FIG. 5 and a GATT write-based affirmative pairing process 604 in FIG. 6, described in greater detail further below and to be implemented by, for example, the device pairing system 100. As described in greater detail below with respect to the embodiments of FIGS. 5-6, the machine readable instructions of the device pairing system 100 may include instructions to establish a connection over a wireless communication channel between the peripheral device 102 and the central device 104; conduct, by the central device 104, a GATT characteristic discovery of a GATT characteristic value of a GATT service (such as of a Device Information Service (DIS)) of the peripheral device 102 over the wireless communication channel; determine an authentication determination prior to device pairing based on determination of a central GATT characteristic value (such as a DIS characteristic value or UUID) to arrive at one of a successful match determination and an unsuccessful match determination; and utilize the central device 104 to send a pairing request to the peripheral device 102 to initiate pairing over the wireless communication channel based upon the GATT characteristic discovery of the GATT characteristic value of the GATT service of the peripheral device 102. In response to the unsuccessful match determination as the authentication determination, the instruction may be to reject the pairing request with the peripheral device 102. The instructions may further be to, in response to the successful match determination as the authentication determination, approve the pairing request with the peripheral device 102 and send a pairing response to the central device 104, and pair the central device 104 and the peripheral device 102 based on the pairing response to create the paired wireless communication channel. In embodiments, the GATT characteristic value of the GATT service of the peripheral device 102 comprises a characteristic value of a Device Information Service (DIS) of the peripheral device 102.

Figure 5:
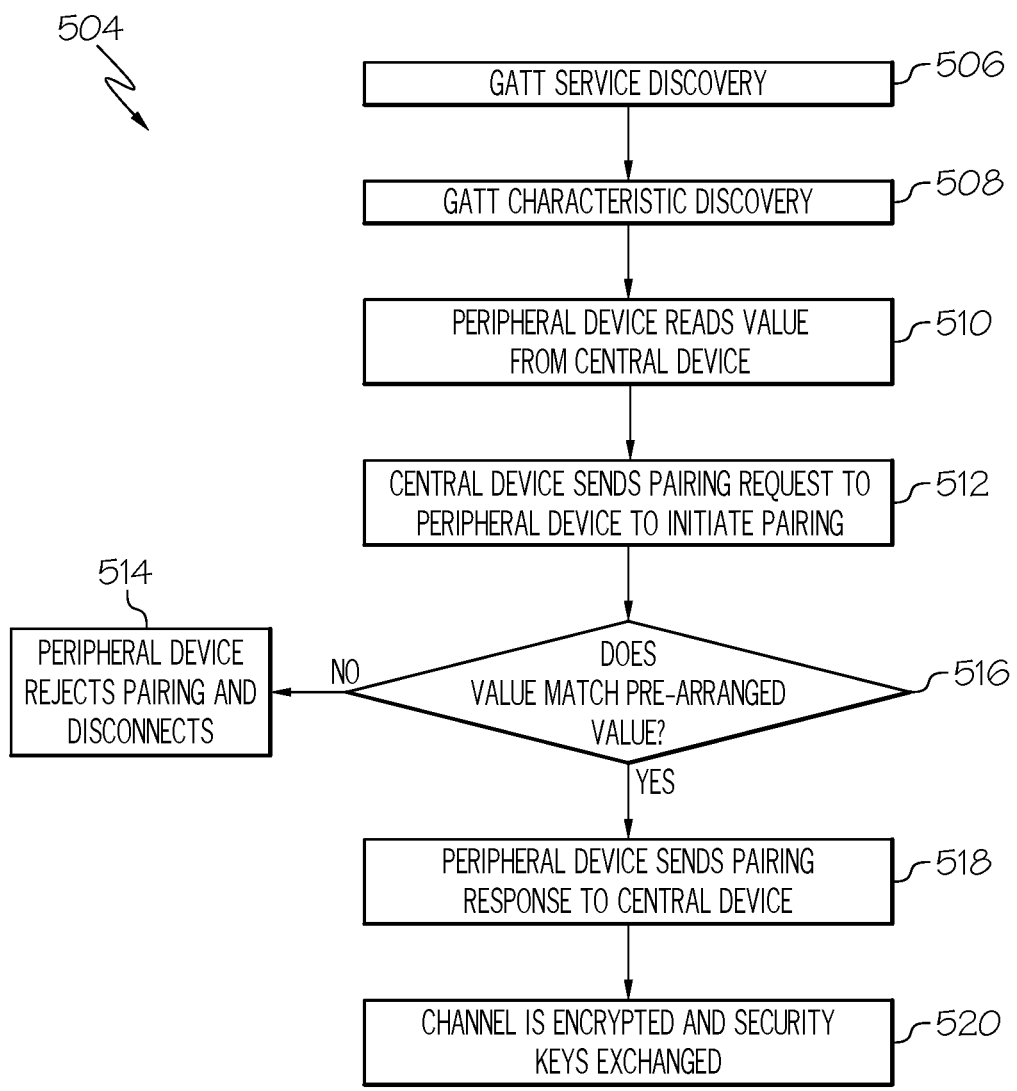
FIG. 5 is a flow chart of a read process for the intermediate affirmative pairing stage of FIG. 2 that may be a Generic Attribute profile (GATT) service and/or characteristic read-based affirmative pairing process to authenticate a pairing initiation prior to permitting submission of a pairing response, according to one or more embodiments shown and described herein.

Referring to FIG. 5, a GATT read-based affirmative pairing process 504, corresponding with one embodiment of the intermediate affirmative pairing stage 204 of FIG. 2, is illustrated. In particular, FIG. 5 illustrates a GATT read-based affirmative pairing process to authenticate a pairing initiation prior to permitting submission of a pairing response, as described in greater detail further below.

In block 506, a GATT service discovery is initiated, and in block 508, a sub-set GATT characteristic discovery is initiated. By way of example and not as a limitation, the central device 104 initiates a GATT service discovery with respect to one or more particular GATT services of the peripheral device 102 in block 506. In block 508, the central device 104 further initiates a GATT service discovery with respect to one or more particular GATT characteristics of the discovered GATT services of the peripheral device 102 from block 506.

In block 510, as a pairing authentication affirmation check, the peripheral device 102 receives and reads a value from the central device 104 (such as from the DIS of the central device 104). In block 512, the central device sends a pairing request to the peripheral device to initiate pairing based on the discovered GATT service(s) and GATT characteristic(s) of blocks 506-508 and the pairing authentication affirmation check of block 510. In an embodiment, a pairing request is rejected when made before the pairing authentication affirmation check of block 510.

The peripheral device 102 may initiate a GATT service discovery with respect to the central device 104 and a GATT characteristic discovery with respect one or more particular GATT characteristics of the central device 104. In at least one embodiment, the peripheral device 102 confirms receipt and a read of at least one discovered central GATT characteristic value such as a DIS characteristic value or UUID of the central device 104. In at least one embodiment, machine readable instructions executed by the one or more processors 1104 may cause the device pairing system 100 to further conduct, by the peripheral device 102, a GATT characteristic discovery of a central characteristic value of a service (such as the DIS) of the central device 104 over the wireless communication channel, read the central characteristic value by the peripheral device 102 to set the central characteristic value as the central GATT characteristic value, and determine the successful match determination based on the central GATT characteristic value matching a pre-arranged value as determined by the peripheral device 102, and determine the unsuccessful match determination based on the central GATT characteristic value not matching a pre-arranged value as determined by the peripheral device 102.

As a non-limiting example, in block 516, the GATT read-based affirmative pairing process 504 determines, through one or more processors 1104, for example, whether the at least one read central GATT characteristic value of the central device 104 matches a pre-arranged value. In at least one embodiment, the pre-arranged value may be input by a developer with respect to the GATT of the peripheral device 102. If not, pairing authentication fails, and the peripheral device 102 rejects the pairing with and disconnects from the central device 104 in block 514. If a match is determined in block 516, the GATT read-based affirmative pairing process 504 continues on to block 518. In block 518, the peripheral device 102 sends a pairing response to the central device 104. In at least one embodiment, the pairing response is indicative of an authenticated pairing and does not require additional required security features for pairing, such as man-in-the middle (MITM) and device bonding. In block 520, the peripheral device 102 and the central device 104 are paired such than a wireless communication channel established therebetween is encrypted and one or more security keys are exchanged between the peripheral device 102 and the central device 104.

With respect to security features as described in this specification, such features may include out-of-band (OOB) security features, MITM security features, and/or bonding security features. As a non-limiting example, use of OOB security features for pairing permits device authentication through use of an OOB channel that permits exchange of large data, such as of up to 128 bits, over the OOB channel to enhance connection security. Requirement of an OOB security feature thus may require usage of such an OOB channel to enhance connection security. The OOB channel may be protected from MITM attacks and may be immune to eavesdropping from unintended wireless devices during the BLE connection with the peripheral device 102 and the central device 104.

MITM attacks may occur where a malicious device impersonates one of the peripheral device 102 and the central device 104 such that the other of the peripheral device 102 and the central device 104 is tricked into connection with the malicious device that may route and control communication between the peripheral device 102 and the central device 104. Thus, the peripheral device 102 and the central device 104 may appear to be validly directly connected without interference while their connection is actually compromised. Requirement of MITM security features requires additional protection by devices against such MITM attacks. Further, a bonding security feature requires an exchange of long-term keys after post-pairing bonding of the peripheral device 102 and the central device 104 and storage of these long-term keys for later use such that encryption may automatically be initiated without pairing subsequent times the peripheral device 102 and the central device 104 connect.

Figure 6:
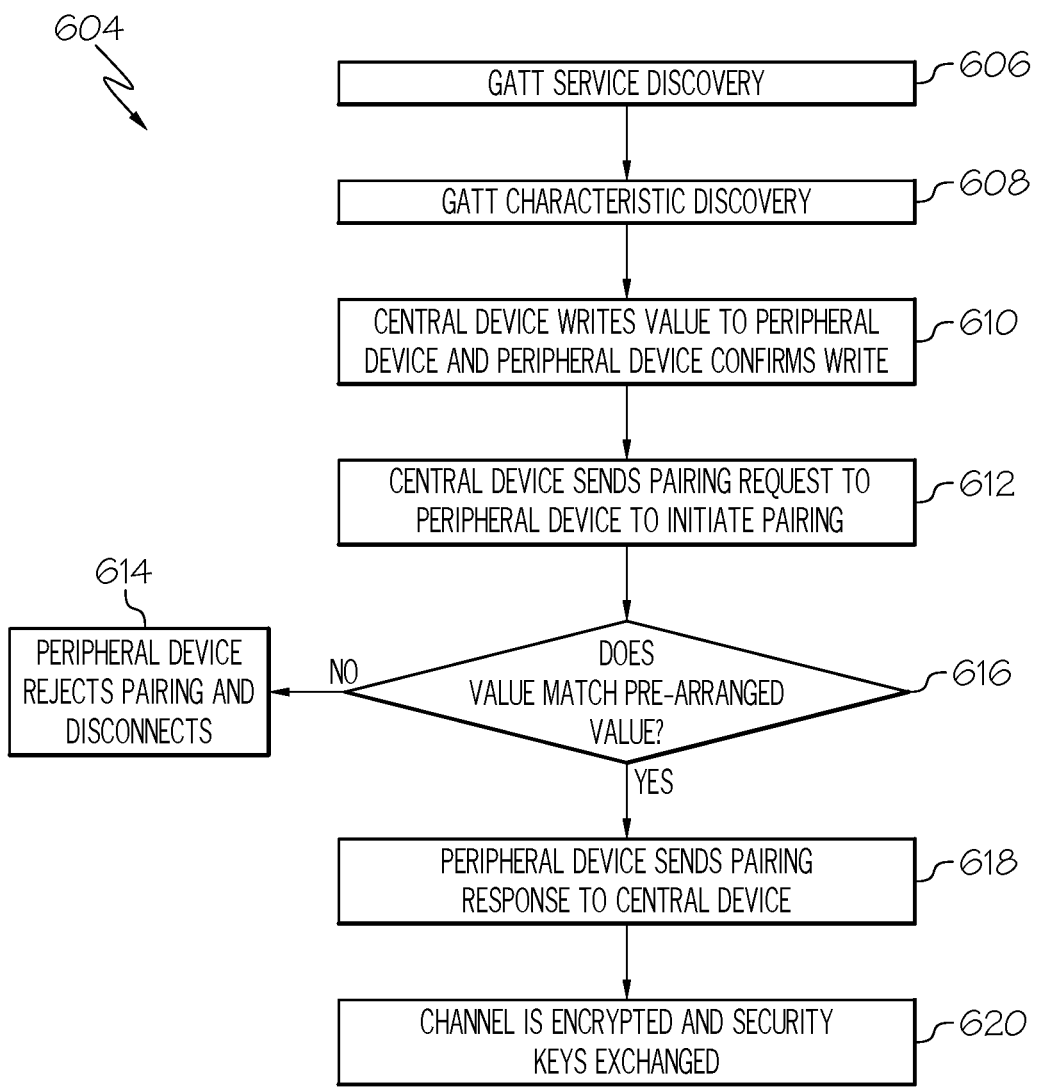
FIG. 6 is a flow chart of a write process for the intermediate affirmative pairing stage of FIG. 2 that may be a GATT service and/or characteristic write-based affirmative pairing process to authenticate a pairing initiation prior to permitting submission of a pairing response, according to one or more embodiments shown and described herein.

Referring to FIG. 6, a GATT write-based affirmative pairing process 604, corresponding with another embodiment of the intermediate affirmative pairing stage 204 of FIG. 2, is illustrated. In particular, FIG. 6 illustrates a GATT write-based affirmative pairing process to authenticate a pairing initiation prior to permitting submission of a pairing response, as described in greater detail further below.

At the start of the GATT write-based affirmative pairing process 604, the peripheral device 102 may start a GATT Write Timer, which may be set to a time period in a range of between about 1 second to about 5 seconds, such as at about 2 seconds. In block 606, a GATT service discovery is initiated, and in block 608, a GATT characteristic discovery is initiated. By way of example and not as a limitation, the central device 104 initiates a GATT service discovery with respect to one or more particular GATT services of the peripheral device 102 in block 606. In block 608, the central device 104 further initiates a GATT service discovery with respect to one or more particular GATT characteristics of the discovered GATT services of the peripheral device 102 from block 606. In block 612, the central device 104 sends a pairing request to the peripheral device 102 to initiate pairing based on the discovered GATT service(s) and GATT characteristic(s) of blocks 606-608 and a pairing authentication affirmation check of block 610, which is described in greater detail below.

In at least one embodiment, machine readable instructions executed by the one or more processors 1104 may cause the device pairing system 100 to further use the central device 104 to write the central GATT characteristic value to the characteristic value of, for example, a DIS of the peripheral device 102, determine the successful match determination based on the central GATT characteristic value matching a pre-arranged value as determined by the peripheral device 102, and determine the unsuccessful match determination based on the central GATT characteristic value not matching a pre-arranged value as determined by the peripheral device 102.

As a non-limiting example, in block 610, the central device 104 writes a central characteristic value to a characteristic value of a GATT service (such as the DIS) of the peripheral device 102, and the peripheral device 102 confirms receipt of the written value and the write to set the central characteristic value as the central GATT characteristic value. In at least one embodiment, the peripheral device 102 confirms receipt of the write to at least one discovered central GATT characteristic value of the peripheral device 102 by the central device 104 that results in at least one written central GATT characteristic value. The written central GATT characteristic value may include or be generated from logic defining at least one of pre-defined data to write to a pre-defined location. As a non-limiting example, the central device 104 may receive a BLE name of the peripheral device 102 and write the same value to a BLE name DIS characteristic value of the peripheral device 102 in block 612. In at least one embodiment, the peripheral device 102 may disable the GATT Write Timer after confirmation of the central GATT characteristic value write from the central device 104.

In block 616, the GATT write-based affirmative pairing process 604 determines, through one or more processors 1104, for example, whether the at least one written central GATT characteristic value of the peripheral device 102 matches a pre-arranged value. In at least one embodiment, the pre-arranged value may be input by a developer with respect to the GATT of the peripheral device 102. If not, such that the central device 104 fails to write a correct central GATT characteristic value to the peripheral device 102, pairing authentication fails. Upon pairing authentication failure, the peripheral device 102 rejects the pairing with and disconnects from the central device 104 in block 614. Thus, a device writing an incorrect central GATT characteristic value to the peripheral device 102 may be rejected for pairing as an unintended device and filtered out as a pairing option.

If a match is determined in block 616, the GATT write-based affirmative pairing process 604 continues on to block 618. In block 618, the peripheral device 102 sends a pairing response to the central device 104. In at least one embodiment, the pairing response is indicative of an authenticated pairing and does not require additional required security features for pairing, such as man-in-the middle (MITM) and device bonding. In block 620, the peripheral device 102 and the central device 104 are paired such than a wireless communication channel established therebetween is encrypted and one or more security keys are exchanged between the peripheral device 102 and the central device 104.

As a non-limiting example, FIGS. 7 and 10 respectively illustrate affirmative pairing processes to authenticate a pairing prior to pairing initiation as a write-based affirmative pairing process 704 in FIG. 7 and an authentication-based affirmative pairing process 1004 in FIG. 10, described in greater detail further below and to be implemented by, for example, the device pairing system 100. As described in greater detail below with respect to the embodiments of FIGS. 7 and 10, the machine readable instructions of the device pairing system 100 may include instructions to send authentication data from the central device 104 to the peripheral device 102 indicative of a first authentication determination; utilize the central device 104 to send a pairing request to the peripheral device 102 to initiate pairing over the wireless communication channel based upon the first authentication determination; and determine a second authentication determination prior to device pairing based on whether the authentication data to indicate the second authentication is successful or unsuccessful. The instructions may further be to, in response to the second authentication determination being unsuccessful, reject the pairing request with the peripheral device 102; in response to the second authentication determination being successful, approve the pairing request with the peripheral device 102 and send a pairing response to the central device 104; and pair the central device 104 and the peripheral device 102 based on the pairing response to create the encrypted wireless communication channel.

Figure 7:
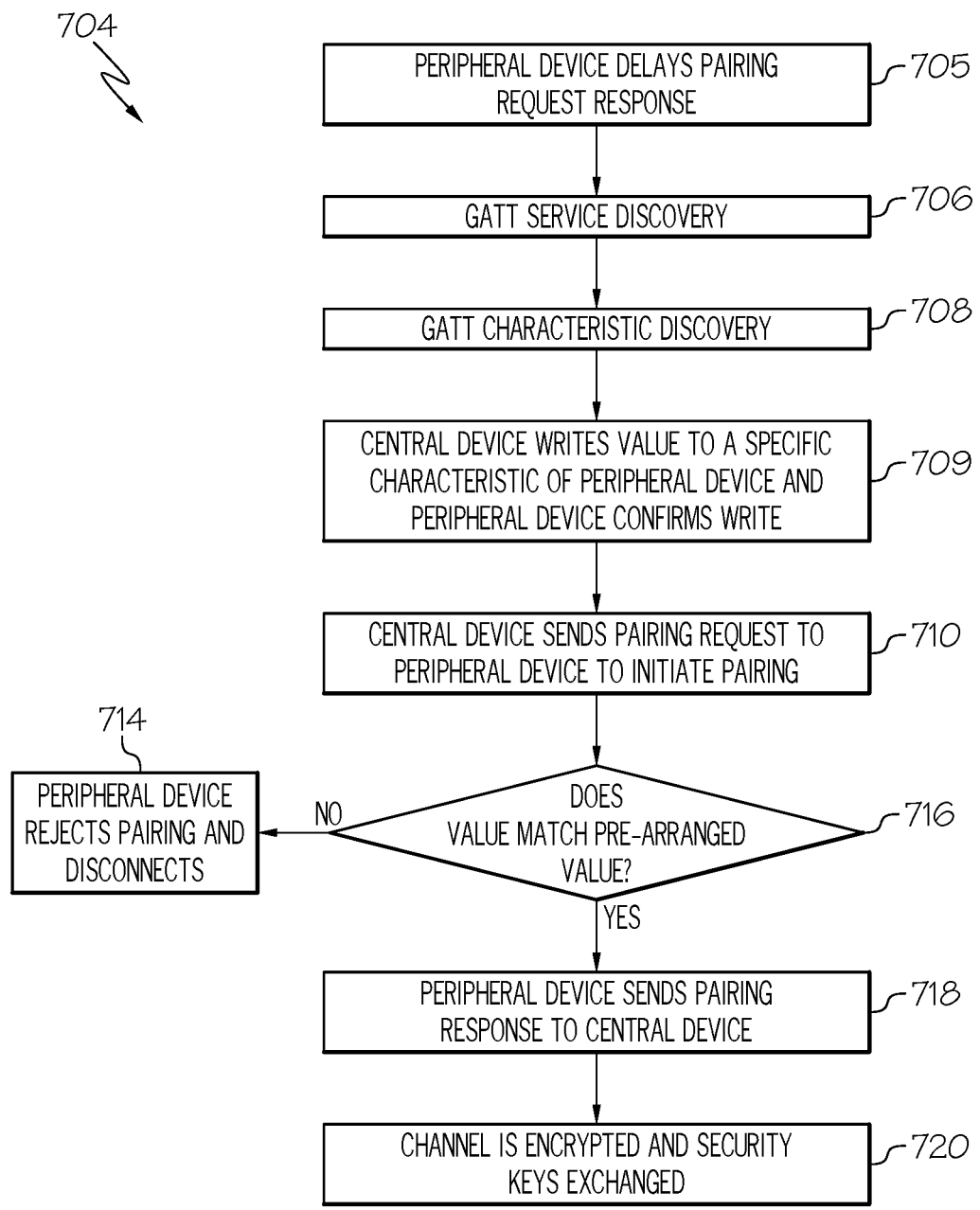
FIG. 7 is a flow chart of another write process for the intermediate affirmative pairing stage of FIG. 2, and in particular a write-based affirmative pairing process to authenticate a pairing prior to pairing initiation, according to one or more embodiments shown and described herein.

Referring to FIG. 7, a write-based affirmative pairing process 704, corresponding with yet another embodiment of the intermediate affirmative pairing stage 204 of FIG. 2, is illustrated. In particular, FIG. 7 illustrates a write-based affirmative pairing process to authenticate a pairing prior to pairing initiation, as described in greater detail below.

Rather than writing to a specific central GATT characteristic value such as a DIS characteristic value as set forth in the GATT write-based affirmative pairing process 604 as described above, the write-based affirmative pairing process 704 implements a write to a specific characteristic of the peripheral device 102 that may be a specified value to a pre-arranged BLE characteristic of the peripheral device. Further, in at least one embodiment with respect to FIG. 7, instructions to send authentication data from the central device 104 to the peripheral device 102 indicative of a first authentication determination may be instructions to write a value by the central device 104 to the characteristic value of the peripheral device 102, wherein a write occurrence is the first authentication determination. The instructions may further be to, as described in greater detail below with respect to FIG. 7, determine whether the value written to the characteristic value of the peripheral device 102 matches a pre-arranged value to arrive at one of a successful match determination indicative of the second authentication determination being successful and an unsuccessful match determination indicative of the second authentication determination being unsuccessful.

At the start of the write-based affirmative pairing process 704, the peripheral device 102 may start a GATT Write Timer, which may be set to a time period in a range of between about 1 second to about 5 seconds, such as at about 2 seconds. In block 705, the peripheral device 102 may set a delay through the GATT Write Timer for a pairing request response. The delay for a pairing request response set in block 705 may take a time period in a range of about 0.1 to 1 second, such as 0.5 seconds, and may be set to a length that includes the length of time associated with implementation of blocks 706-709. In block 710, the central device 104 sends a pairing request to the peripheral device 102 to initiate pairing based on the discovered GATT service(s) and GATT characteristic(s) and the write of blocks 706-709.

In block 706, a GATT service discovery is initiated, and in block 708, a sub-GATT characteristic discovery is initiated. By way of example and not as a limitation, the central device 104 initiates a GATT service discovery with respect to one or more particular GATT services of the peripheral device 102 in block 706. In block 708, the central device 104 further initiates a GATT service discovery with respect to one or more particular GATT characteristics of the discovered GATT services of the peripheral device 102 from block 706.

In block 709, the central device 104 writes a pre-arranged value to a specific characteristic of the peripheral device 102, and the peripheral device 102 confirms receipt of the written value and the write. In at least one embodiment, the peripheral device 102 confirms receipt and the write to the specific characteristic value of the peripheral device 102 by the central device 104 that results in at least one written GATT characteristic value. As a non-limiting example, central device 104 will write the pre-arranged value to a pre-arranged characteristic of the peripheral device 102 per the BLUETOOTH® Core Specification.

In at least one embodiment, the peripheral device 102 may disable the GATT Write Timer after confirmation of the characteristic value write from the central device 104. Such a write action assists with notifying the peripheral device 102 that the central device 104 is an appropriate, intended device with which to pair. The peripheral device 102 may reject the pairing with the central device if the peripheral device 102 does not confirm the write, indicative of a failure of the central device 104 to write a value to the peripheral device in block 709.

In block 716, the write-based affirmative pairing process 704 determines, through one or more processors 1104, for example, whether the at least one written GATT characteristic value of the peripheral device 102 matches a pre-arranged value. In at least one embodiment, the pre-arranged value may be input by a developer with respect to the GATT of the peripheral device 102. If not, such that the central device 104 fails to write a correct GATT characteristic value to the peripheral device 102, pairing authentication fails. Upon pairing authentication failure, the peripheral device 102 rejects the pairing with and disconnects from the central device 104 in block 714. Thus, a device writing an incorrect GATT characteristic value to the peripheral device 102 may be rejected for pairing as an unintended device and filtered out as a pairing option.

If a match is determined in block 716, the write-based affirmative pairing process 704 continues on to block 718. In block 618, the peripheral device 102 sends a pairing response to the central device 104 indicative of an authenticated pairing. In block 720, the peripheral device 102 and the central device 104 are paired such than a wireless communication channel established therebetween is encrypted and one or more security keys are exchanged between the peripheral device 102 and the central device 104.

Figure 8:
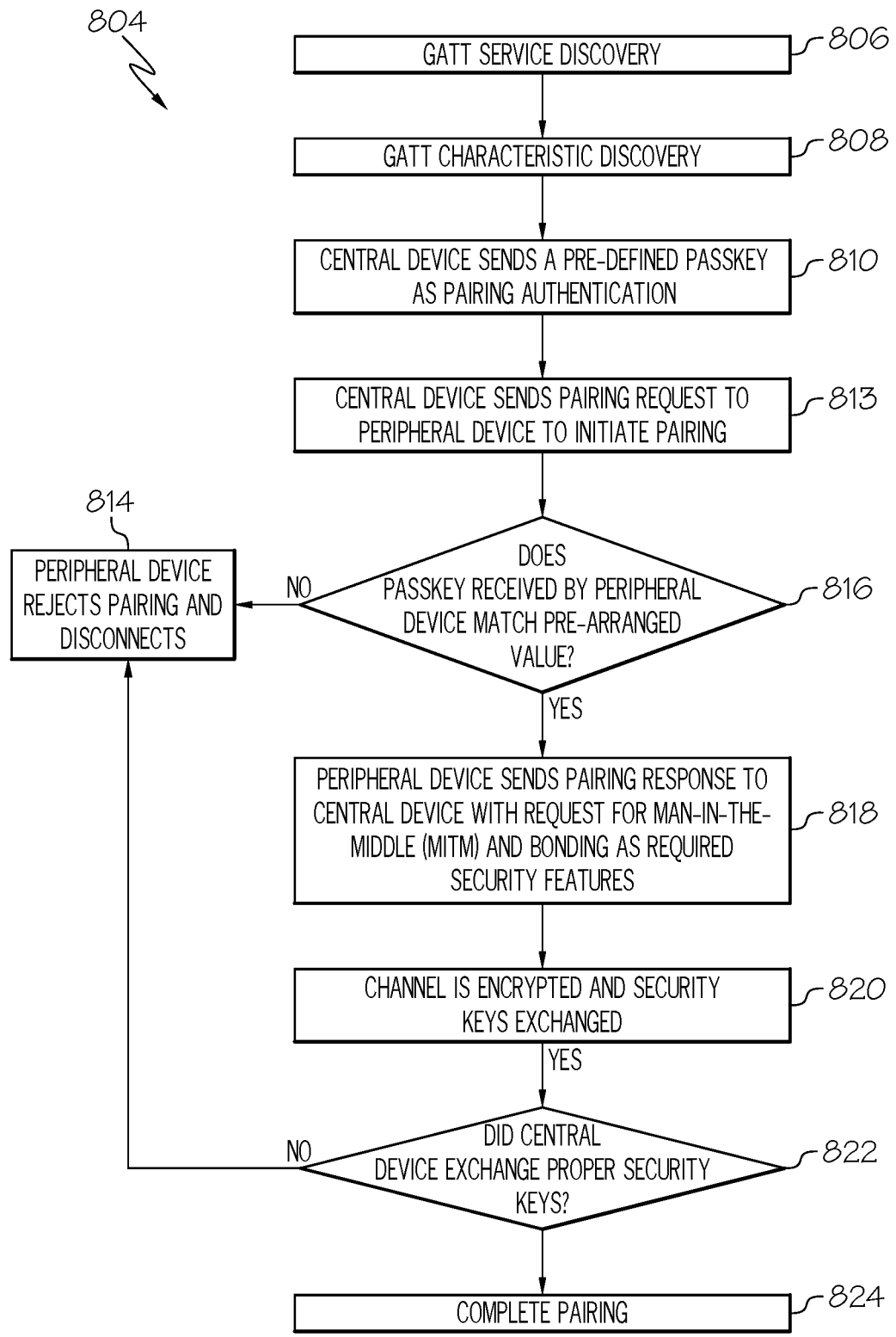
FIG. 8 is a flow chart of an association model process for the intermediate affirmative pairing stage of FIG. 2, and showing an example of a passkey-based affirmative pairing process to authenticate a pairing initiation prior to permitting submission of a pairing response, according to one or more embodiments shown and described herein.

As a non-limiting example, FIGS. 8-9 respectively illustrate association model requested feature based affirmative pairing processes such as a passkey-based affirmative pairing process 804 in FIG. 8 and an out-of-band (OOB) based affirmative pairing process 904 in FIG. 9, described in greater detail further below and to be implemented by, for example, the device pairing system 100. As described in greater detail below with respect to the embodiments of FIGS. 8-9, the machine readable instructions of the device pairing system 100 may include instructions to conduct, by the central device, a GATT characteristic discovery of a characteristic value of the peripheral device 102 over the wireless communication channel; send a requested feature from the central device 104 to the peripheral device 102 to determine an authentication determination; determine the authentication determination prior to device pairing based on whether the requested feature received by the peripheral device is correct to arrive at one of a successful determination and an unsuccessful match determination; and utilize the central device 104 to send a pairing request to the peripheral device 102 to initiate pairing over the wireless communication channel based upon the GATT characteristic discovery of the characteristic value (such as of the DIS) of the peripheral device 102 and the authentication determination.

In response to an incorrect finding for the authentication determination, the instruction may be to reject the pairing request with the peripheral device 102. The instructions may further comprise in response to a correct finding for the authentication determination as the authentication determination, send an initial pairing response including a security request to approve the pairing request with the peripheral device 102 and proceed to a second authentication determination. The instructions may further include instructions to determine in the second authentication determination whether the central device exchanged proper security keys with the peripheral device in response to the security request; in response to a negative finding for the second authentication determination, reject the pairing request with the peripheral device; and in response to a positive finding for the second authentication determination, complete the pairing between the peripheral device and the central device to create the paired wireless communication channel. In embodiments, the requested feature is a pre-defined value of an association model, non-limiting examples of which are described below in greater detail. The instructions may further be to determine the authentication determination prior to device pairing based on whether the requested feature received by the peripheral device 102 is correct to arrive at one of a successful determination and an unsuccessful match determination comprises instructions to determine whether the pre-defined value of the association model received by the peripheral device 102 matches an expected value of the association model Referring to FIG. 8, an association model process such as a passkey-based affirmative pairing process 804, corresponding with yet another embodiment of the intermediate affirmative pairing stage 204 of FIG. 2, is illustrated. In particular, FIG. 8 illustrates a passkey-based affirmative pairing process to authenticate a pairing initiation prior to permitting submission of a pairing response and in which the requested feature is a pre-defined passkey, as described in greater detail below.

In a manual user method, the peripheral device 102 would generate a random 6 digit pin to be displayed for the user to take and enter as a pairing code to confirm the pairing on a display screen of the central device 104. Such a method of having end users enter a pairing code to authenticate pairing may result in issues such as user error and additional time taken to complete a pairing.

The passkey-based affirmative pairing process 804 permits an automated authentication through a code approach in which a fixed code is used for the passkey code that the central device 104 will send to the peripheral device 102, as described in greater detail below. As a non-limiting example, the peripheral device 102 will request the BLE passkey and the central device 104 will send the fixed code as a static 6 digit code to confirm the pairing. Thus, an end user will not need to manually enter the passkey, and the passkey code would be static for all such pairings between the central device 104 and the peripheral device 102. Alternatively, the passkey may be a dynamic value based on information exchanged between the central device 104 and the peripheral device 102 when connected, such as a serial number of the peripheral device 102 as determined from a GATT characteristic discovery as described below, for example. Logic from the peripheral device 102, such as logic implemented through the one or more processors 1104, may further define rules to determine an automated code generation for the central device 104 to send to the peripheral device 102 as a pre-defined passkey value.

In block 806, a GATT service discovery is initiated, and in block 808, a sub-set GATT characteristic discovery is initiated. By way of example and not as a limitation, the central device 104 initiates a GATT service discovery with respect to one or more particular GATT services of the peripheral device 102 in block 806. In block 808, the central device 104 further initiates a GATT characteristic discovery with respect to one or more particular GATT characteristics of the discovered GATT services of the peripheral device 102 from block 806. In block 813, the central device 104 sends a pairing request to the peripheral device 102 to initiate pairing based on the discovered GATT service(s) and GATT characteristic(s) of blocks 806-808 and a pairing authentication affirmation check of block 810.

In block 810, the central device 104 sends a pre-defined passkey to authenticate the pairing to the peripheral device 102. The central device 104 should also send a security response to the security request for the one or more additional required security features, such as submission of the one or more additional required security features.

In block 816, the passkey-based affirmative pairing process 804 determines, through one or more processors 1104, for example, whether the pre-defined passkey received by the peripheral device 102 matches a pre-arranged value. In at least one embodiment, the pre-arranged value may be input by a developer with respect to the peripheral device 102. If not, such that the central device 104 fails to send a passkey, or fails to send a correct passkey, to the peripheral device 102, pairing authentication fails. Upon pairing authentication failure, the peripheral device 102 rejects the pairing with and disconnects from the central device 104 in block 814. Thus, a device sending an incorrect passkey or failing to send a passkey to the peripheral device 102 may be rejected for pairing as an unintended device and filtered out as a pairing option.

If a match is determined in block 816, the passkey-based affirmative pairing process 804 continues on to block 818. In block 818, the peripheral device 102 sends a pairing response to the central device 104 along with a security request for one or more additional required security features such as for MITM and bonding. In block 820, the peripheral device 102 and the central device 104 are paired such that a wireless communication channel established therebetween is encrypted and one or more security keys are exchanged between the peripheral device 102 and the central device 104. In block 822, the passkey-based affirmative pairing process 804 determines, through one or more processors 1104, for example, whether the central device 104 exchanged proper security keys with the peripheral device 102. If not, the peripheral device 102 rejects the pairing in block 814. In at least one embodiment, a display screen of the peripheral device 102 and/or the central device 104 may display a rejection message, such as "pairing rejected" or "pump not found," if the passkey-based affirmative pairing process 804 determines that the central device 104 did not exchange proper security keys with the peripheral device 102.

If so, the pairing is completed between the peripheral device 102 and the central device 104 in block 824. As a non-limiting example, in the block 813, the central device 104 should have sent the security response to the security request for the one or more additional required security features, such as MITM and bonding. If the appropriate security response was sent, the pairing is completed in block 824. Otherwise, the pairing is rejected in block 814.

Figure 9:
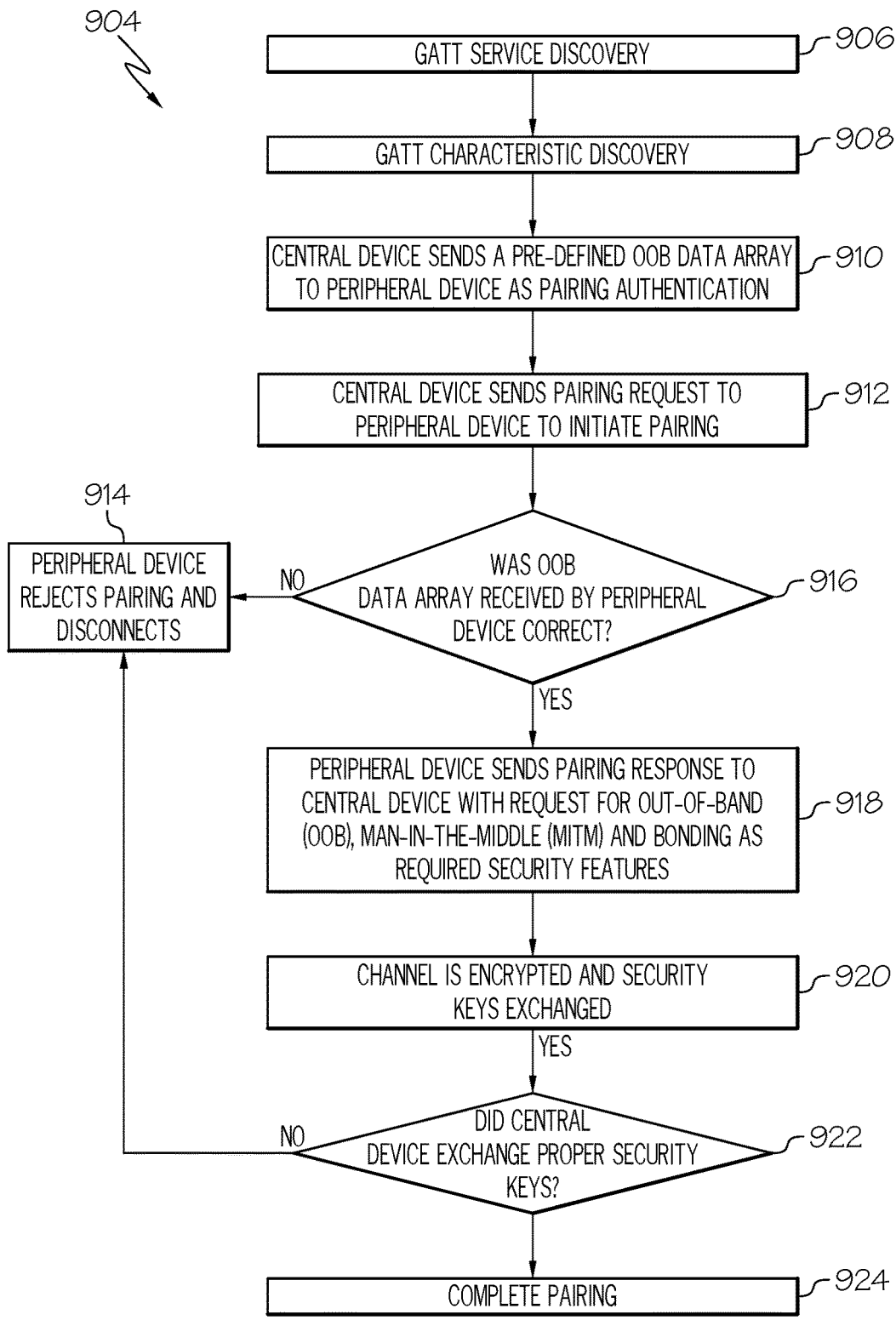
FIG. 9 is a flow chart of an out-of-band (OOB) security feature authentication process for the intermediate affirmative pairing stage of FIG. 2, and in particular an OOB-based affirmative pairing process to authenticate a pairing initiation prior to permitting submission of a pairing response, according to one or more embodiments shown and described herein.

Referring to FIG. 9, an OOB-based affirmative pairing process 904, corresponding with yet one other embodiment of the intermediate affirmative pairing stage 204 of FIG. 2, is illustrated. In particular, FIG. 9 illustrates an OOB-based affirmative pairing process to authenticate a pairing initiation prior to receiving a pairing response and in which the requested feature is a pre-defined OOB data array, as described in greater detail below.

With the OOB-based affirmative pairing process 904, the central device 104 and the peripheral device 102 could use OOB data as a mechanism for the central device 104 to correctly identify itself to the peripheral device 102, as described in greater detail below. As a non-limiting example, the central device 104 would send a pairing request to and attempt to pair with the peripheral device 102. In return, the peripheral device 102 would respond with a security request that OOB, MITM, and bonding security features are required. The central device 104 would then be required to respond to the security request with a security response including at least a pre-defined OOB data array, as described in greater detail below, to authenticate pairing.

With respect to the OOB-based affirmative pairing process 904, in block 906, a GATT service discovery is initiated, and in block 908, a GATT characteristic discovery is initiated. By way of example and not as a limitation, the central device 104 initiates a GATT service discovery with respect to one or more particular GATT services of the peripheral device 102 in block 906. In block 908, the central device 104 further initiates a GATT service discovery with respect to one or more particular GATT characteristics of the discovered GATT services of the peripheral device 102 from block 906. In block 912, the central device 104 sends a pairing request to the peripheral device 102 to initiate pairing based on the discovered GATT service(s) and GATT characteristic(s) of blocks 906-908 and a pairing authentication affirmation check of block 910.

In block 910, the central device 104 sends a pre-defined out-of-band (OOB) data array to authenticate the pairing to the peripheral device 102. The central device 104 should also send a security response to the additional security request for the one or more additional required security features, such as submission of the one or more additional required security features.

In block 916, the OOB-based affirmative pairing process 904 determines, through one or more processors 1104, for example, whether the pre-defined OOB data array received by the peripheral device 102 matches an expected OOB data array and is correct. In at least one embodiment, the expected OOB data array may be input by a developer with respect to the peripheral device 102. If not, such that the central device 104 fails to send pre-defined OOB data array, or fails to send a correct pre-defined OOB data array, to the peripheral device 102, pairing authentication fails. Upon pairing authentication failure, the peripheral device 102 rejects the pairing with and disconnects from the central device 104 in block 914. Thus, a device sending an incorrect pre-defined OOB data array or failing to send a pre-defined OOB data array to the peripheral device 102 may be rejected for pairing as an unintended device and filtered out as a pairing option.

If a correct submission of the pre-defined OOB data array is determined in block 916, the OOB-based affirmative pairing process 904 continues on to block 918. In block 918, the peripheral device 102 sends a pairing response to the central device 104 along with a security request for an OOB security feature as well as one or more additional required security features such as for MITM and bonding.

In block 920, the peripheral device 102 and the central device 104 are paired such than a wireless communication channel established therebetween is encrypted and one or more security keys are exchanged between the peripheral device 102 and the central device 104.

In block 922, the OOB-based affirmative pairing process 904 determines, through one or more processors 1104, for example, whether the central device 104 exchanged proper security keys with the peripheral device 102. If not, the peripheral device 102 rejects the pairing in block 914. If so, the pairing is completed between the peripheral device 102 and the central device 104 in block 924. As a non-limiting example, in the block 912, the central device 104 should have sent the security response to the security request for the one or more additional required security features, such as MITM and bonding in addition to the pre-defined OOB data array. If the appropriate security response was sent, the pairing is completed in block 824. Otherwise, the pairing is rejected in block 914.

Figure 10:
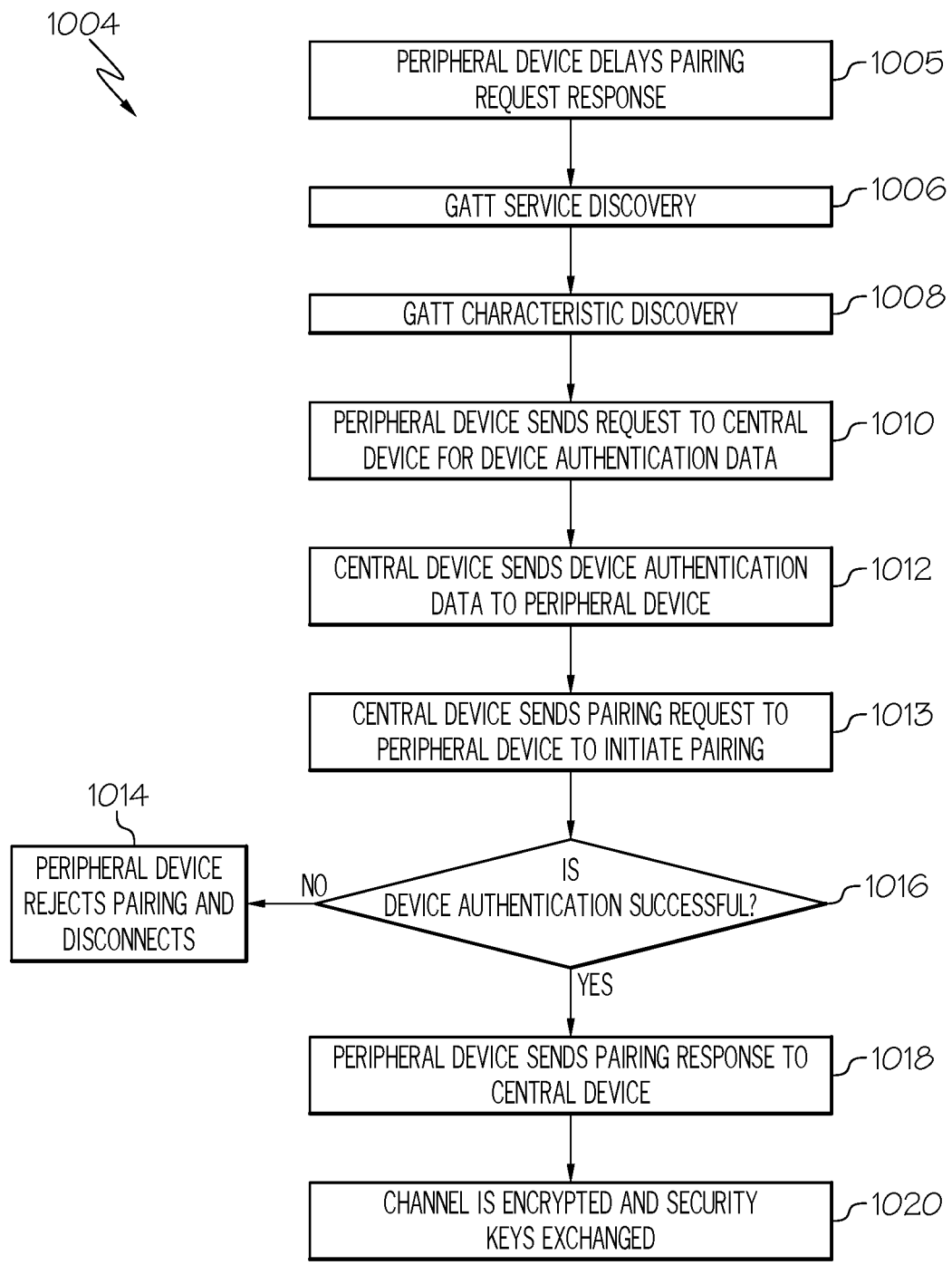
FIG. 10 is a flow chart of a device authentication process for the intermediate affirmative pairing stage of FIG. 2, and in particular an authentication-based affirmative pairing process to authenticate a pairing prior to pairing initiation, according to one or more embodiments shown and described herein.

Referring to FIG. 10, an authentication-based affirmative pairing process 1004, corresponding with one another embodiment of the intermediate affirmative pairing stage 204 of FIG. 2, is illustrated. In particular, FIG. 10 illustrates an authentication-based affirmative pairing process to authenticate a pairing prior to pairing initiation, as described in greater detail below.

Rather than reading or writing to a specific characteristic value as set forth in the affirmative pairing processes 504-704, or sending a passkey or OOB data array as set forth in the affirmative pairing processes 804-904 as described above, the authentication-based affirmative pairing process 1004 implements a device authentication such as a device key exchange. In at least one embodiment, the device key exchange includes device authentication data as a device key indicative of an authenticated device to permit an authentication by the peripheral device 102 of the central device 104 as a desired, acceptable, authenticated device with which to pair prior to the central device 104 initiating pairing with the peripheral device 102. Further, in at least one embodiment with respect to FIG. 10, instructions to send device authentication data in response to a request for device authentication data from the peripheral device.

At the start of the authentication-based affirmative pairing process 1004, the peripheral device 102 may start an authentication timer set for a time period in a range of from about 1 second to 5 seconds, such as for 2 seconds. In block 1005, the peripheral device 102 may set a delay for a pairing request response. The delay for a pairing request response set in block 1005 may take a time period in a range of about 0.1 to 1 second, such as 0.5 seconds, and may be set to a length that includes the length of time associated with implementation of blocks 1006-1008.

In block 1006, a GATT service discovery is initiated, and in block 1008, a GATT characteristic discovery is initiated. By way of example and not as a limitation, the central device 104 initiates a GATT service discovery with respect to one or more particular GATT services of the peripheral device 102 in block 1006. In block 1008, the central device 104 further initiates a GATT characteristic discovery with respect to one or more particular GATT characteristics of the discovered GATT services of the peripheral device 102 from block 1006. The time to implement blocks 1005 to 1008 may take between around 0.1 seconds to around 1 second, such as around 0.5 seconds.

In blocks 1010-1012, a device key exchange permits an authentication by the peripheral device 102 of the central device 104 as a desired, acceptable device with which to pair prior to the central device 104 initiating pairing with the peripheral device 102 in block 1013. As a non-limiting example, in block 1010, the peripheral device 102 sends a request to the central device 104 for device authentication data. In block 1012, central device 104 sends the device authentication data to the peripheral device 102. Alternatively, the central device 104 may directly send device authentication data to the peripheral device 102 without responding to a request for such data. After block 1012, the peripheral device 102 may disable the authentication timer.

In at least one embodiment, the peripheral device 102 may disable the authentication timer after confirmation of the central device 104 sending device authentication data to the peripheral device 102 in block 1012. Such an authentication data submission of block 1012 assists with notifying the peripheral device 102 that the central device 104 is an appropriate, intended device with which to pair. The peripheral device 102 may reject the pairing with the central device 104 if the peripheral device 102 does not confirm the authentication data submission of block 1012, indicative of a failure of the central device 104 to provide the authentication data to the peripheral device in block 1012.

In block 1013, the central device 104 sends a pairing request to the peripheral device 102 to initiate pairing based on the discovered GATT service(s) and GATT characteristic (s) and the device authentication of blocks 1006-1012.

In block 1016, the authentication-based affirmative pairing process 1004 determines, through one or more processors 1104, for example, whether the device authentication data sent to the peripheral device 102 in block 1012 by the central device 104 results in a successful device authentication, such as when the submitted device authentication data in block 1012 matches pre-arranged device authentication data as determined by the peripheral device 102. In at least one embodiment, the pre-arranged value device authentication data or rules regarding a successful device authentication may be input by a developer with respect to the peripheral device 102. If not, such that the central device 104 fails to provide correct device authentication data in block 1012 to result in a successful device authentication in block 1016, pairing authentication fails. Upon pairing authentication failure, the peripheral device 102 rejects the pairing with and disconnects from the central device 104 in block 1014. Thus, a device not submitting device authentication data in block 1012 or not submitting correct device authentication data to result in a successful device authentication in block 1016 may be rejected for pairing as an unintended device and filtered out as a pairing option.

If a successful device authentication match is determined in block 1016, the authentication-based affirmative pairing process 1004 continues on to block 1018. In block 1018, the peripheral device 102 sends a pairing response to the central device 104 indicative of an authenticated pairing. In block 1020, the peripheral device 102 and the central device 104 are paired such than a wireless communication channel established therebetween is encrypted and one or more security keys are exchanged between the peripheral device 102 and the central device 104.

Figure 11:
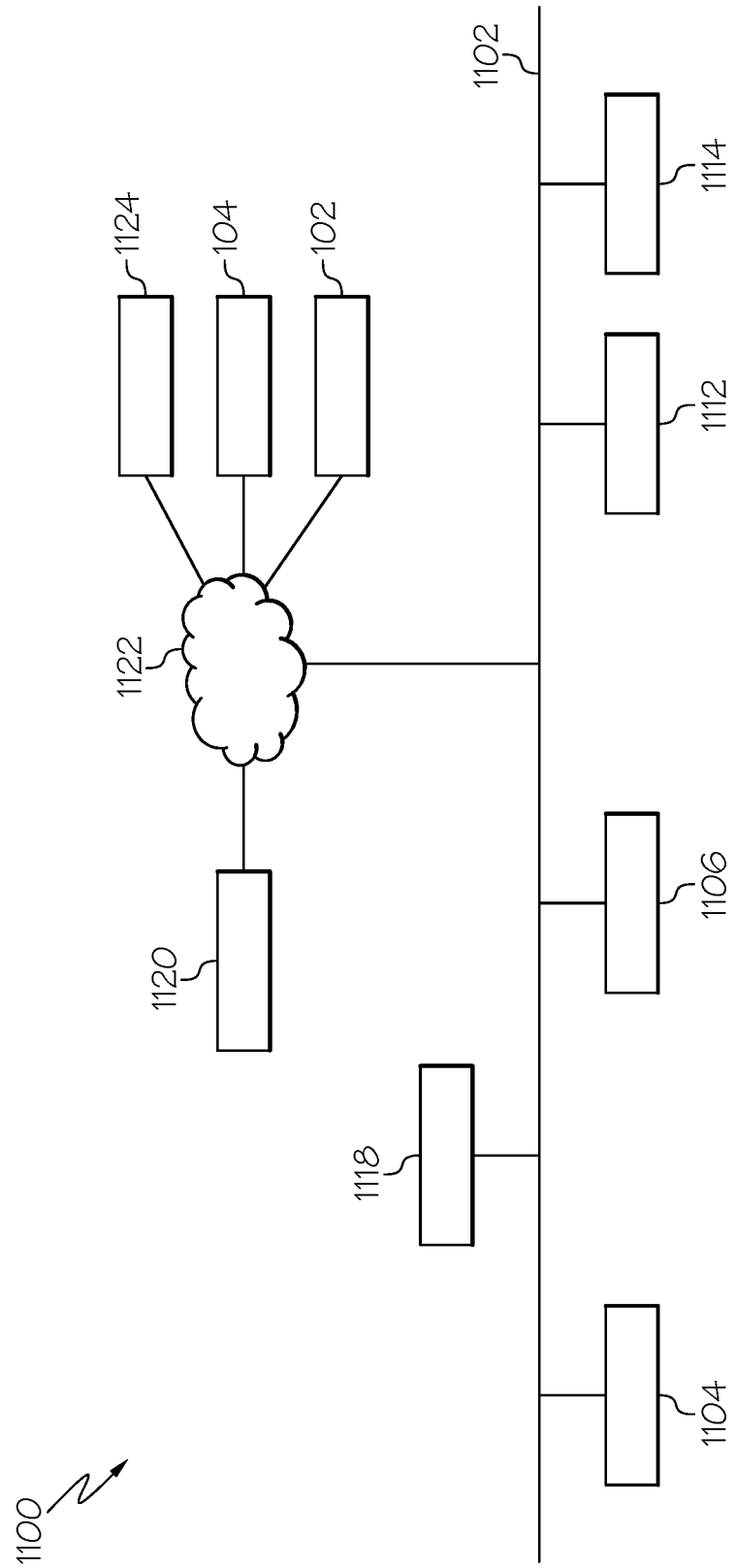
FIG. 11 schematically illustrates a system for implementing computer and software based methods to utilize the affirmative pairing systems and methods of FIGS. 1-10, according to one or more embodiments shown and described herein.

Referring to FIG. 11, a system 1100 for implementing a computer and software-based method to utilize the device pairing system as associated stages, as shown in FIGS. 1-10, is illustrated and may be implemented along with using a graphical user interface (GUI) 1124 that is accessible at a user workstation, e.g., a computing device and/or at the peripheral and central devices 102, 104, that may be medical devices, for example. The system 1100 includes a communication path 1102, one or more processors 1104, one or more memory components 1106, a profile component 1112, a storage or database 1114, a network interface hardware 1118, a server 1120, a network 1122, devices 102, 104, and at least one GUI 1124. The various components of the system 1100 and the interaction thereof will be described in detail below.

While only one application server 1120 and one GUI 1124 that may be part of a workstation is illustrated, the system 1100 can include multiple workstations and application servers containing one or more applications that can be located at geographically diverse locations across a plurality of industrial sites. In some embodiments, the system 1100 is implemented using a wide area network (WAN) or network 1122, such as an intranet or the Internet, or other wired or wireless communication network that may include a cloud computing-based network configuration (for example, "the cloud"). The workstation computer 324 may include digital systems and other devices permitting connection to and navigation of the network. Other system 1100 variations allowing for communication between various geographically diverse components are possible. The lines depicted in FIG. 11 indicate communication rather than physical connections between the various components.

As noted above, the system 1100 includes the communication path 1102. The communication path 1102 may be formed from any medium that is capable of transmitting a signal such as, for example, conductive wires, conductive traces, optical waveguides, or the like, or from a combination of mediums capable of transmitting signals. The communication path 1102 communicatively couples the various components of the system 1100. As used herein, the term "communicatively coupled" means that coupled components are capable of exchanging data signals with one another such as, for example, electrical signals via conductive medium, electromagnetic signals via air, optical signals via optical waveguides, and the like.

As noted above, the system 1100 includes the one or more processors 1104. The one or more processors 1104 can be any device capable of executing machine readable instructions. Accordingly, the one or more processors 1104 may be a controller, an integrated circuit, a microchip, a computer, or any other computing device. The one or more processors 1104 is communicatively coupled to the other components of the system 1100 by the communication path 1102. Accordingly, the communication path 302 may communicatively couple any number of processors with one another, and allow the modules coupled to the communication path 1102 to operate in a distributed computing environment. Specifically, each of the modules can operate as a node that may send and/or receive data. The one or more processors 1104 may process the input signals received from the system modules and/or extract information from such signals.

As noted above, the system 1100 includes the one or more memory components 1106 which is coupled to the communication path 1102 and communicatively coupled to the processor 304. The one or more memory components 1106 may be a non-transitory computer readable medium or non-transitory computer readable memory and may be configured as a nonvolatile computer readable medium. The one or more memory components 1106 may comprise RAM, ROM, flash memories, hard drives, or any device capable of storing machine readable instructions such that the machine readable instructions can be accessed and executed by the one or more processors 1104. The machine readable instructions may comprise logic or algorithm(s) written in any programming language such as, for example, machine language that may be directly executed by the processor, or assembly language, object-oriented programming (OOP), scripting languages, microcode, etc., that may be compiled or assembled into machine readable instructions and stored on the one or more memory components 1106. Alternatively, the machine readable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components. In embodiments, the system 1100 may include the one or more processors 1104 communicatively coupled to the one or more memory components 1106 that stores instructions that, when executed by the one or more processors 1104, cause the processor to perform one or more functions as described herein.

Still referring to FIG. 11, as noted above, the system 1100 comprises the display such as a GUI 1124 on a screen of a computing device for providing visual output such as, for example, information, graphical reports, messages, or a combination thereof. The computing device, such as devices 102, 104, may include one or more computing devices across platforms, or may be communicatively coupled to devices across platforms, such as mobile smart devices including smartphones, tablets, laptops, and/or the like or medical devices such as blood glucose meters, insulin pumps, continuous glucose monitors, and the like. The display on the screen of the computing device is coupled to the communication path 1102 and communicatively coupled to the one or more processors 1104. Accordingly, the communication path 1102 communicatively couples the display to other modules of the system 1100. The display can include any medium capable of transmitting an optical output such as, for example, a cathode ray tube, light emitting diodes, a liquid crystal display, a plasma display, or the like. Additionally, it is noted that the display or the computing device such as device 102, 104 can include at least one of the one or more processors 1104 and the one or more memory components 1106. While the system 1100 is illustrated as a single, integrated system in FIG. 11, in other embodiments, the systems can be independent systems.

The system 1100 comprises the profile component 1112 that in at least one embodiment is representative of the BLE architecture with respect to the GATT each of the peripheral device 102 and the central device 104 as described herein. The profile component 1112 is coupled to the communication path 1102 and communicatively coupled to the one or more processors 1104. As will be described in further detail below, the one or more processors 1104 may process the input signals received from the system modules and/or extract information from such signals.

The system 1100 includes the network interface hardware 1118 for communicatively coupling the system 1100 with a computer network such as network 1122. The network interface hardware 1118 is coupled to the communication path 1102 such that the communication path 1102 communicatively couples the network interface hardware 1118 to other modules of the system 1100. The network interface hardware 1118 can be any device capable of transmitting and/or receiving data via a wireless network. Accordingly, the network interface hardware 1118 can include a communication transceiver for sending and/or receiving data according to any wireless communication standard. For example, the network interface hardware 1118 can include a chipset (e.g., antenna, processors, machine readable instructions, etc.) to communicate over wired and/or wireless computer networks such as, for example, wireless fidelity (Wi-Fi), WiMax, BLUETOOTH®, IrDA, Wireless USB, Z-Wave, ZigBee, or the like.

Still referring to FIG. 11, data from various applications running on computing devices such as devices 102, 104 can be provided from the devices 102, 104 to the system 1100 via the network interface hardware 1118. The computing device can be any device having hardware (e.g., chipsets, processors, memory, etc.) for communicatively coupling with the network interface hardware 1118 and a network 1122. Specifically, the computing device can include an input device having an antenna for communicating over one or more of the wireless computer networks described above.

The network 1122 can include any wired and/or wireless network such as, for example, wide area networks, metropolitan area networks, the Internet, an Intranet, the cloud, satellite networks, or the like. Accordingly, the network 1122 can be utilized as a wireless access point by the computer 1124 to access one or more servers (e.g., a server 1120). The server 1120 and any additional servers generally include processors, memory, and chipset for delivering resources via the network 1122. Resources can include providing, for example, processing, storage, software, and information from the server 1120 to the system 1100 via the network 1122. Additionally, it is noted that the server 1120 and any additional servers can share resources with one another over the network 1122 such as, for example, via the wired portion of the network, the wireless portion of the network, or combinations thereof.

Item 1. A device pairing system including a peripheral device, a central device, the device pairing system configured to pair the peripheral device and the central device to establish a paired wireless communication channel therebetween, one or more processors, one or more memory components communicatively coupled to the one or more processors, and machine readable instructions stored in the one or more memory components that cause the device pairing system to perform at least the following when executed by the one or more processors: establish a connection over a wireless communication channel between the peripheral device and the central device; conduct, by the central device, a GATT characteristic discovery of a GATT characteristic value of a GATT service of the peripheral device over the wireless communication channel; determine an authentication determination prior to device pairing based on determination of a central GATT characteristic value to arrive at one of a successful match determination and an unsuccessful match determination; utilize the central device to send a pairing request to the peripheral device to initiate pairing over the wireless communication channel based upon the GATT characteristic discovery of the GATT characteristic value of the GATT service of the peripheral device; in response to the unsuccessful match determination as the authentication determination, reject the pairing request with the peripheral device; in response to the successful match determination as the authentication determination, approve the pairing request with the peripheral device and send a pairing response to the central device; and pair the central device and the peripheral device based on the pairing response to create the paired wireless communication channel.

Item 2. The device pairing system of item 1, wherein the GATT characteristic value of the GATT service of the peripheral device comprises a characteristic value of a Device Information Service (DIS) of the peripheral device.

Item 3. The device pairing system of item 1 or 2, wherein instructions to determine an authentication determination prior to device pairing based on determination of a central GATT characteristic value of the central device to arrive at one of a successful match determination and an unsuccessful match determination comprises instructions to: conduct, by the peripheral device, a GATT characteristic discovery of a central characteristic value of the central device over the wireless communication channel; read the central characteristic value by the peripheral device to set the central characteristic value as the central GATT characteristic value; determine the successful match determination based on the central GATT characteristic value matching a pre-arranged value as determined by the peripheral device; and determine the unsuccessful match determination based on the central GATT characteristic value not matching a pre-arranged value as determined by the peripheral device.

Item 4. The device pairing system of item 3, wherein the central characteristic value is one of a DIS characteristic value or a Universal Unique Identifier (UUID).

Item 5. The device pairing system of items 1 or 2, wherein instructions to determine an authentication determination prior to device pairing based on determination of a central GATT characteristic value to arrive at one of a successful match determination and an unsuccessful match determination comprises instructions to: use the central device to write the a central characteristic value to a characteristic value of the peripheral device to set the central characteristic value as the central GATT characteristic value; determine the successful match determination based on the central GATT characteristic value matching a pre-arranged value as determined by the peripheral device; and determine the unsuccessful match determination based on the central GATT characteristic value not matching a pre-arranged value as determined by the peripheral device.

Item 6. The device pairing system of item 5, wherein the central characteristic value is one of a DIS characteristic value or a Universal Unique Identifier (UUID).

Item 7. The device pairing system of any of items 1 to 6, wherein the central GATT characteristic value comprises a serial number of the peripheral device submitted from the peripheral device to the central device.

Item 8. The device pairing system of item 7, further comprising instructions to transmit the serial number of the peripheral device from the peripheral device to the central device over the wireless communication channel.

Item 9. The device pairing system of items 1 or 2, wherein the instructions further comprise instructions to exchange one or more security key features between the central device and the peripheral device prior to pairing the central device and the peripheral device.

Item 10. The device pairing system of item 9, further comprising instructions to bond the peripheral device and the central device such that after pairing the peripheral device and the central device store the one or more security key features that are exchanged.

Item 11. The device pairing system of any of items 1 to 10, further comprising instructions to disconnect the peripheral device and the central device after bonding.

Item 12. The device pairing system of any of items 1 to 11, wherein the instructions to establish a connection over a wireless communication channel between the peripheral device and the central device further comprise instructions to place each of the peripheral device and the central device in a pairing mode.

Item 13. The device pairing system of any of items 1 to 12, further comprising instructions to: start an authentication timer at the start of the GATT characteristic discovery; disable the authentication timer in response to the successful match determination as the authentication determination; and display a pairing confirmation on a respective display screen of each of the central device and the peripheral device after pairing the central device and the peripheral device based on the pairing response.

Item 14. A device pairing system including a peripheral device, a central device, the device pairing system configured to pair the peripheral device and the central device to establish a paired wireless communication channel therebetween, one or more processors, one or more memory components communicatively coupled to the one or more processors, and machine readable instructions stored in the one or more memory components that cause the device pairing system to perform at least the following when executed by the one or more processors: establish a connection over a wireless communication channel between the peripheral device and the central device; conduct, by the central device, a GATT characteristic discovery of a characteristic value of the peripheral device over the wireless communication channel; send a requested feature from the central device to the peripheral device to determine an authentication determination; determine the authentication determination prior to device pairing based on whether the requested feature received by the peripheral device is correct to arrive at one of a successful determination and an unsuccessful match determination; utilize the central device to send a pairing request to the peripheral device to initiate pairing over the wireless communication channel based upon the GATT characteristic discovery of the peripheral device and the authentication determination; in response to an incorrect finding for the authentication determination, reject the pairing request with the peripheral device; in response to a correct finding for the authentication determination, send an initial pairing response by the peripheral device including a security request and proceed to a second authentication determination; determine in the second authentication determination whether the central device exchanged proper security keys with the peripheral device in response to the security request; in response to a negative finding for the second authentication determination, reject the pairing request with the peripheral device; and in response to a positive finding for the second authentication determination, complete the pairing between the peripheral device and the central device to create the paired wireless communication channel.

Item 15. The device pairing system of item 14, wherein the security request is for at least one of a man-in-the-middle (MITM) security feature and a bonding security feature.

Item 16. The device pairing system of items 14 or 15, wherein the requested feature is a pre-defined passkey.

Item 17. The device pairing system of item 16, wherein instructions to determine the authentication determination prior to device pairing based on whether the requested feature received by the peripheral device is correct to arrive at one of a successful determination and an unsuccessful match determination comprises instructions to determine whether the pre-defined passkey received by the peripheral device matches a pre-arranged value.

Item 18. The device pairing system of items 14 or 15, wherein the requested feature is a pre-defined out-of-band (OOB) data array.

Item 19. The device pairing system of item 18, wherein instructions to determine the authentication determination prior to device pairing based on whether the requested feature received by the peripheral device is correct to arrive at one of a successful determination and an unsuccessful match determination comprises instructions to determine whether the pre-defined OOB data array received by the peripheral device matches an expected OOB data array.

Item 20. The device pairing system of items 14 or 15, wherein the requested feature is a pre-defined value of an association model, and instructions to determine the authentication determination prior to device pairing based on whether the requested feature received by the peripheral device is correct to arrive at one of a successful determination and an unsuccessful match determination comprises instructions to determine whether the pre-defined value of the association model received by the peripheral device matches an expected value of the association model.

Item 21. The device pairing system of any of items 14 to 20, further comprising instructions to, in response to a negative finding for the second authentication determination, display a message indicative of the rejection of the pairing request on a display screen of the peripheral device.

Item 22. A device pairing system including a peripheral device, a central device, the device pairing system configured to pair the peripheral device and the central device to establish a paired wireless communication channel therebetween, one or more processors, one or more memory components communicatively coupled to the one or more processors, and machine readable instructions stored in the one or more memory components that cause the device pairing system to perform at least the following when executed by the one or more processors: establish a connection over a wireless communication channel between the peripheral device and the central device; conduct, by the central device, a GATT characteristic discovery of a characteristic value of the peripheral device over the wireless communication channel; send authentication data from the central device to the peripheral device indicative of a first authentication determination; utilize the central device to send a pairing request to the peripheral device to initiate pairing over the wireless communication channel based upon the first authentication determination; determine a second authentication determination prior to device pairing based on whether the authentication data to indicate the second authentication is successful or unsuccessful; in response to the second authentication determination being unsuccessful, reject the pairing request with the peripheral device; in response to the second authentication determination being successful, approve the pairing request with the peripheral device and send a pairing response to the central device; and pair the central device and the peripheral device based on the pairing response to create the paired wireless communication channel.

Item 23. The device pairing system of item 22, wherein the instructions to send authentication data from the central device to the peripheral device indicative of a first authentication determination comprise instructions to write a value by the central device to the characteristic value of the peripheral device, wherein a write occurrence comprises the first authentication determination.

Item 24. The device pairing system of item 23, wherein the instructions to determine a second authentication determination prior to device pairing based on whether the authentication data to indicate the second authentication is successful or unsuccessful comprise instructions to determine whether the value written to the characteristic value of the peripheral device matches a pre-arranged value to arrive at one of a successful match determination indicative of the second authentication determination being successful and an unsuccessful match determination indicative of the second authentication determination being unsuccessful.

Item 25. The device pairing system of item 22, wherein the instructions to send authentication data from the central device to the peripheral device indicative of a first authentication determination comprise instructions to send device authentication data in response to a request for device authentication data from the peripheral device.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

It is noted that the terms "substantially" and "about" and "approximately" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Unless defined otherwise, all technical and scientific terms used herein have the same meanings as is commonly understood by one of skill in the art to which this disclosure belongs. As used herein, the articles "a" and "an" refer to one or more than one (i.e., at least one) of the grammatical object of the article. By way of example, "an element" means one element or more than one element.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A device pairing system comprising:
a peripheral device;
a central device, the device pairing system configured to pair the peripheral device and the central device to establish a paired wireless communication channel therebetween;
one or more processors;
one or more memory components communicatively coupled to the one or more processors; and
machine readable instructions stored in the one or more memory components that cause the device pairing system to perform at least the following when executed by the one or more processors:

establish a connection over a wireless communication channel between the peripheral device and the central device;

conduct, by the central device, a Generic Attribute profile (GATT) characteristic discovery of a GATT characteristic value of a GATT service of the peripheral device over the wireless communication channel;

determine an authentication determination prior to device pairing based on determination of a central GATT characteristic value to arrive at one of a successful match determination and an unsuccessful match determination;

utilize the central device to send a pairing request to the peripheral device to initiate pairing over the wireless communication channel based upon the GATT characteristic discovery of the GATT characteristic value of the GATT service of the peripheral device;

in response to the unsuccessful match determination as the authentication determination, reject the pairing request with the peripheral device;

in response to the successful match determination as the authentication determination, approve the pairing request with the peripheral device and send a pairing response to the central device; and pair the central device and the peripheral device based on the pairing response to create the paired wireless communication channel.

2. The device pairing system of claim 1, wherein the GATT characteristic value of the GATT service of the peripheral device comprises a characteristic value of a Device Information Service (DIS) of the peripheral device.

3. The device pairing system of claim 1, wherein instructions to determine an authentication determination prior to device pairing based on determination of a central GATT characteristic value of the central device to arrive at one of a successful match determination and an unsuccessful match determination comprises instructions to:

conduct, by the peripheral device, a GATT characteristic discovery of a central characteristic value of the central device over the wireless communication channel;

read the central characteristic value by the peripheral device to set the central characteristic value as the central GATT characteristic value;

determine the successful match determination based on the central GATT characteristic value matching a pre-arranged value as determined by the peripheral device; and determine the unsuccessful match determination based on the central GATT characteristic value not matching a pre-arranged value as determined by the peripheral device.

4. The device pairing system of claim 3, wherein the central characteristic value is one of a DIS characteristic value or a Universal Unique Identifier (UUID).

5. The device pairing system of claim 1, wherein instructions to determine an authentication determination prior to device pairing based on determination of a central GATT characteristic value to arrive at one of a successful match determination and an unsuccessful match determination comprises instructions to:

use the central device to write the a central characteristic value to a characteristic value of the peripheral device to set the central characteristic value as the central GATT characteristic value;

determine the successful match determination based on the central GATT characteristic value matching a pre-arranged value as determined by the peripheral device; and determine the unsuccessful match determination based on the central GATT characteristic value not matching a pre-arranged value as determined by the peripheral device.

6. The device pairing system of claim 5, wherein the central characteristic value is one of a DIS characteristic value or a Universal Unique Identifier (UUID).

7. The device pairing system of claim 5, wherein the central GATT characteristic value comprises a serial number of the peripheral device submitted from the peripheral device to the central device.

8. The device pairing system of claim 7, further comprising instructions to transmit the serial number of the peripheral device from the peripheral device to the central device over the wireless communication channel.

9. The device pairing system of claim 1, wherein the instructions further comprise instructions to exchange one or more security key features between the central device and the peripheral device prior to pairing the central device and the peripheral device.

10. The device pairing system of claim 9, further comprising instructions to bond the peripheral device and the central device such that after pairing the peripheral device and the central device store the one or more security key features that are exchanged.

11. The device pairing system of claim 10, further comprising instructions to disconnect the peripheral device and the central device after bonding.

12. The device pairing system of claim 1, wherein the instructions to establish a connection over a wireless communication channel between the peripheral device and the central device further comprise instructions to place each of the peripheral device and the central device in a pairing mode.

13. The device pairing system of claim 1, further comprising instructions to:

start an authentication timer at the start of the GATT characteristic discovery;

disable the authentication timer in response to the successful match determination as the authentication determination; and display a pairing confirmation on a respective display screen of each of the central device and the peripheral device after pairing the central device and the peripheral device based on the pairing response.

14. A device pairing system comprising:

a peripheral device;

a central device, the device pairing system configured to pair the peripheral device and the central device to establish a paired wireless communication channel therebetween;

one or more processors;

one or more memory components communicatively coupled to the one or more processors; and machine readable instructions stored in the one or more memory components that cause the device pairing system to perform at least the following when executed by the one or more processors:

establish a connection over a wireless communication channel between the peripheral device and the central device;

conduct, by the central device, a Generic Attribute profile (GATT) characteristic discovery of a characteristic value of the peripheral device over the wireless communication channel;
send a requested feature from the central device to the peripheral device to determine an authentication determination;
determine the authentication determination prior to device pairing based on whether the requested feature received by the peripheral device is correct to arrive at one of a successful determination and an unsuccessful match determination;
utilize the central device to send a pairing request to the peripheral device to initiate pairing over the wireless communication channel based upon the GATT characteristic discovery of the peripheral device and the authentication determination;
in response to an incorrect finding for the authentication determination, reject the pairing request with the peripheral device;
in response to a correct finding for the authentication determination, send an initial pairing response by the peripheral device including a security request and proceed to a second authentication determination;
determine in the second authentication determination whether the central device exchanged proper security keys with the peripheral device in response to the security request;
in response to a negative finding for the second authentication determination, reject the pairing request with the peripheral device; and
in response to a positive finding for the second authentication determination, complete the pairing between the peripheral device and the central device to create the paired wireless communication channel.

15. The device pairing system of claim 14, wherein the security request is for at least one of a man-in-the-middle (MITM) security feature and a bonding security feature.

16. The device pairing system of claim 14, wherein the requested feature is a pre-defined passkey.

17. The device pairing system of claim 16, wherein instructions to determine the authentication determination prior to device pairing based on whether the requested feature received by the peripheral device is correct to arrive at one of a successful determination and an unsuccessful match determination comprises instructions to determine whether the pre-defined passkey received by the peripheral device matches a pre-arranged value.

18. The device pairing system of claim 14, wherein the requested feature is a pre-defined out-of-band (OOB) data array.

19. The device pairing system of claim 18, wherein instructions to determine the authentication determination prior to device pairing based on whether the requested feature received by the peripheral device is correct to arrive at one of a successful determination and an unsuccessful match determination comprises instructions to determine whether the pre-defined OOB data array received by the peripheral device matches an expected OOB data array.

20. The device pairing system of claim 14, wherein the requested feature is a pre-defined value of an association model, and instructions to determine the authentication determination prior to device pairing based on whether the requested feature received by the peripheral device is correct to arrive at one of a successful determination and an unsuccessful match determination comprises instructions to determine whether the pre-defined value of the association model received by the peripheral device matches an expected value of the association model.

21. The device pairing system of claim 14, further comprising instructions to, in response to a negative finding for the second authentication determination, display a message indicative of the rejection of the pairing request on a display screen of the peripheral device.

22. A device pairing system comprising:
a peripheral device;
a central device, the device pairing system configured to pair the peripheral device and the central device to establish a paired wireless communication channel therebetween;
one or more processors;
one or more memory components communicatively coupled to the one or more processors;
machine readable instructions stored in the one or more memory components that cause the device pairing system to perform at least the following when executed by the one or more processors:
establish a connection over a wireless communication channel between the peripheral device and the central device;
conduct, by the central device, a Generic Attribute profile (GATT) characteristic discovery of a characteristic value of the peripheral device over the wireless communication channel;
send authentication data from the central device to the peripheral device indicative of a first authentication determination;
utilize the central device to send a pairing request to the peripheral device to initiate pairing over the wireless communication channel based upon the first authentication determination;
determine a second authentication determination prior to device pairing based on whether the authentication data to indicate the second authentication is successful or unsuccessful;
in response to the second authentication determination being unsuccessful, reject the pairing request with the peripheral device;
in response to the second authentication determination being successful, approve the pairing request with the peripheral device and send a pairing response to the central device; and
pair the central device and the peripheral device based on the pairing response to create the paired wireless communication channel.

23. The device pairing system of claim 22, wherein the instructions to send authentication data from the central device to the peripheral device indicative of a first authentication determination comprise instructions to write a value by the central device to the characteristic value of the peripheral device, wherein a write occurrence comprises the first authentication determination.

24. The device pairing system of claim 23, wherein the instructions to determine a second authentication determination prior to device pairing based on whether the authentication data to indicate the second authentication is successful or unsuccessful comprise instructions to determine whether the value written to the characteristic value of the peripheral device matches a pre-arranged value to arrive at one of a successful match determination indicative of the second authentication determination being successful and an unsuccessful match determination indicative of the second authentication determination being unsuccessful.

25. The device pairing system of claim 22, wherein the instructions to send authentication data from the central device to the peripheral device indicative of a first authentication determination comprise instructions to send device authentication data in response to a request for device authentication data from the peripheral device.

* * * * *